*(12)* United States Patent
Arata et al.

(10) Patent No.: US 11,419,778 B2
(45) Date of Patent: Aug. 23, 2022

(54) TWO-DEGREE-OF-FREEDOM ROTATION MECHANISM USING PARALLEL SPRINGS

(71) Applicant: KYUSHU UNIVERSITY, NATIONAL UNIVERSITY CORPORATION, Fukuoka (JP)

(72) Inventors: Jumpei Arata, Fukuoka (JP); Makoto Hashizume, Fukuoka (JP)

(73) Assignee: KYUSHU UNIVERSITY, NATIONAL UNIVERSITY CORPORATION

( * ) Notice: Subject to any disclaimer, the term of this patent is extended or adjusted under 35 U.S.C. 154(b) by 607 days.

(21) Appl. No.: 16/307,293

(22) PCT Filed: Jun. 5, 2017

(86) PCT No.: PCT/JP2017/020881
§ 371 (c)(1),
(2) Date: Dec. 5, 2018

(87) PCT Pub. No.: WO2017/213106
PCT Pub. Date: Dec. 14, 2017

(65) Prior Publication Data
US 2019/0133551 A1 May 9, 2019

(30) Foreign Application Priority Data
Jun. 7, 2016 (JP) .............................. JP2016-113880

(51) Int. Cl.
*A61H 1/02* (2006.01)
*B25J 11/00* (2006.01)
(Continued)

(52) U.S. Cl.
CPC ................ *A61H 1/02* (2013.01); *A61B 8/00* (2013.01); *A61B 8/42* (2013.01); *B25J 11/00* (2013.01);
(Continued)

(58) Field of Classification Search
CPC .......... A61H 1/02; A61H 1/0237–0296; A61H 23/02; A61H 2001/0207;
(Continued)

(56) References Cited

U.S. PATENT DOCUMENTS 6,042,555 A    3/2000  Kramer et al.
6,050,962 A    4/2000  Kramer et al.
(Continued)

FOREIGN PATENT DOCUMENTS

JP    2005-169011 A    6/2005
JP    4065459 B2      3/2008
(Continued)

OTHER PUBLICATIONS

J. Arata et al., "Outer Shell Type 2 DOF Bending Manipulator Using Spring-Link Mechanism for Medical Applications", 2010 IEEE International Conference on Robotics and Automation, held May 3-8, 2010 in Anchorage, Alaska, published by IEEE, Piscataway, NJ, pp. 1041-1046, (May 2010).
(Continued)

*Primary Examiner* — Rachel T Sippel
(74) *Attorney, Agent, or Firm* — Harness, Dickey & Pierce, P.L.C.

(57) ABSTRACT

A manipulator includes a base body, a first link supported to be capable of advancing and retracting with respect to the base body, a first leaf spring connected to a tip of the first link as a rotation pair by a first base end pin, a second link that is arranged with the first link side by side and is supported to be capable of advancing and retracting with respect to the base body, a second leaf spring connected to a tip of the second link as a rotation pair by a second base end pin in the same direction as the first base end pin, and a driven link that is connected to tips of the first and second leaf springs as rotation pairs by first and second tip pins in
(Continued)

the same direction as the first and second base end pins, respectively.

9 Claims, 18 Drawing Sheets

(51) Int. Cl.
*F16H 21/16* (2006.01)
*B25J 17/02* (2006.01)
*A61B 8/00* (2006.01)

(52) U.S. Cl.
CPC ............ *B25J 17/02* (2013.01); *B25J 17/0258* (2013.01); *F16H 21/16* (2013.01)

(58) Field of Classification Search
CPC ........ A61H 2201/0157; A61H 2201/12; A61H 2201/1207; A61H 2201/123; A61H 2201/1635–1638; A61H 2201/1664–1666; A61H 2201/1676; A61H 2205/06; A61H 2205/065; B25J 11/00; B25J 17/02; B25J 17/0258; F16H 21/16
See application file for complete search history.

(56) References Cited

U.S. PATENT DOCUMENTS

| | | | |
|---|---|---|---|
| 6,110,130 | A | 8/2000 | Kramer |
| 6,413,229 | B1 | 7/2002 | Kramer et al. |
| 6,428,490 | B1 | 8/2002 | Kramer et al. |
| 7,084,884 | B1 | 8/2006 | Nelson et al. |
| 2001/0020140 | A1 | 9/2001 | Kramer |
| 2003/0083596 | A1 | 5/2003 | Kramer et al. |
| 2004/0236541 | A1 | 11/2004 | Kramer et al. |
| 2005/0273027 | A1* | 12/2005 | Farrell ............... A63B 23/16 602/21 |
| 2008/0039892 | A1 | 2/2008 | Mitsuishi et al. |
| 2008/0195005 | A1* | 8/2008 | Horst ............... A61H 1/0218 601/22 |
| 2009/0144664 | A1 | 6/2009 | Kramer et al. |
| 2009/0276058 | A1 | 11/2009 | Ueda et al. |
| 2012/0059291 | A1* | 3/2012 | Nguyen ............. A61H 1/0288 601/40 |
| 2013/0031764 | A1 | 2/2013 | Sarh et al. |
| 2013/0338556 | A1* | 12/2013 | Hoffman .......... A63B 21/00069 602/22 |
| 2017/0348852 | A1 | 12/2017 | Sarh et al. |

FOREIGN PATENT DOCUMENTS

| | | |
|---|---|---|
| JP | 4460890 B2 | 5/2010 |
| JP | 2013-035120 A | 2/2013 |
| JP | 2014-161477 A | 9/2014 |
| WO | WO-99-21478 A1 | 5/1999 |
| WO | WO-2007-043308 A1 | 4/2007 |
| WO | WO-2010-117051 A1 | 10/2010 |

OTHER PUBLICATIONS

Extended European Search Report for Patent Application No. EP 17810281.0, dated Feb. 26, 2020 (7 pages).
Japanese Office Action for Patent Application No. JP 2016-113880, dated Jan. 28, 2020 (5 pages).
International Search Report for PCT/JP2017/020881; dated Aug. 29, 2017 (5 pages).
Written Opinion for PCT/JP2017/020881; dated Aug. 29, 2017 (11 pages).
Guthart, Gary S. and J. Kenneth Salisbury, Jr.: "The Intuitive™ Telesurgery System: Overview and Application"; Proceedings of the 2000 IEEE International Conference on Robotics & Automation; San Francisco, CA; Apr. 2000; (pp. 618-621).
Japanese Office Action for corresponding Application No. JP 2016-113880 dated Jun. 2, 2020 with English translation (5 pages).
European Office Action for corresponding Application No. 17810281.0 dated May 10, 2022 (7 Pages).

* cited by examiner

TWO-DEGREE-OF-FREEDOM ROTATION MECHANISM USING PARALLEL SPRINGS

BACKGROUND

Technical Field

The present invention relates to a two-degree-of-freedom rotation mechanism using parallel springs.

Related Art

As a manipulator used for intra-operative laparoscopic ultrasonic diagnosis or a forearm motion support device used for improving rehabilitation effect, an apparatus adopting mechanical elements such as wire mechanism and link mechanism is known, for example.

As products of multi-degree-of-freedom manipulators of this type, for example, "da Vinci surgical system" by Intuitive Surgical Inc. is known (see Gary S. Guthart and J. Kenneth Salisbury, Jr., "The Intuitive (TM) Telesurgery System: Overview and Application", Proceedings of the 2000 IEEE International Conference on Robotics & Automation San Francisco, Calif. April 2000, pp. 618-621, 2000). In the multi-degree-of-freedom manipulator in The Intuitive (TM) Telesurgery System: Overview and Application, wire is adopted as a tool for transmitting power from a driving device. By winding up the wire around the driving device, bending of a joint and opening and closing of a grip portion are realized.

Examples of the related art of a multi-degree-of-freedom manipulator include Japanese Patent No. 4460890 or the like. In the multi-degree-of-freedom manipulator disclosed in Japanese Patent No. 4460890, link mechanism is adopted as a tool for transmitting power from a driving device.

Examples of the related art of a rehabilitation apparatus include Japanese Patent No. 4065459 or the like. In a movement support apparatus disclosed in Japanese Patent No. 4065459, a rubber artificial muscle, which is an actuator, is disposed between a plurality of cuffs attached at a position of a palm across a wrist joint. The rubber artificial muscle helps movement of the wrist in the direction of palmar flexion. As the rubber artificial muscle, for example, a McKiben-type pneumatic actuator including a cylinder portion including a pneumatic valve and a sleeve portion, which is also called a McKiben-type pneumatic rubber artificial muscle, is used.

However, there are following problems in wire driving as a power transmission method adopted in The Intuitive (TM) Telesurgery System: Overview and Application.

First, since there is a risk of "elongation", "break", or the like, wire needs to be replaced frequently. For example, in the "da Vinci surgical system" described above, wire replacement is required for about every ten operations. Since the wire is wound around a plurality of gears and pulleys, it takes a great deal of trouble in detaching and mounting. This leads to an increase in running cost and maintenance load.

Secondly, since the wire expands and contracts, there is a limit to control precision of a joint and a grip portion. There is also a disadvantage that the wire can transmit power only in one direction (i.e., a drawing direction).

Third, there is a problem that it is difficult to sterilize and clean the wire. Therefore, in the multi-degree-of-freedom manipulator in the related art, pre-operative and post-operative sterilization and cleaning operations are very complicated.

There is a following problem in link mechanism as a power transmission method adopted in Japanese Patent No. 4460890.

First, when a plurality of link mechanisms including a plurality of links are provided, the number of parts increases, so it is difficult to reduce size and weight, and product cost increases. This problem also applies to a configuration using the pneumatic actuator of Japanese Patent No. 4065459.

Secondly, if the rotation operation is performed by a plurality of link mechanisms, a bending radius (in other words, a swinging radius) of a capturing device (for example, a first support body 16 of Japanese Patent No. 4460890) increases, and it is difficult to make a smooth movement for approaching an affected part in surgery performed on a limited narrow part, as in an ultrasonic diagnosis in a laparoscopic surgery, for example. This problem also occurs in a wire drive mechanism using gears or pulleys, and a pneumatic actuator as well.

The present invention has been devised in view of the above-described circumstances in the related art, and an object of the present invention is to provide a two-degree-of-freedom rotation mechanism using parallel springs, which is lightweight, has a small number of parts and a simple structure, is capable of operating a driven link with two-degree-of-freedom at low cost, is excellent in sterilizing and disinfecting property, and does not apply excessive burden to a target.

SUMMARY OF THE INVENTION

According to the present invention, there is provided a two-degree-of-freedom rotation mechanism using parallel springs, including: a base body; a first link that is supported to be capable of advancing and retracting in a longitudinal direction of the first link with respect to the base body; a first leaf spring of a rectangular shape of which a longitudinal base end is connected to a tip of the first link as a rotation pair by a first base end pin penetrating in a thickness direction of the first leaf spring; a second link that is arranged with the first link side by side, and is supported to be capable of advancing and retracting in a longitudinal direction of the second link with respect to the base body; a second leaf spring of a rectangular shape of which a longitudinal base end is connected to a tip of the second link as a rotation pair by a second base end pin penetrating in a thickness direction of the second leaf spring in the same direction as the first base end pin; and a driven link that is connected to a tip of the first leaf spring as a rotation pair by a first tip pin in the same direction as the first base end pin and connected to a tip of the second leaf spring as a rotation pair by a second tip pin in the same direction as the second base end pin.

According to the two-degree-of-freedom rotation mechanism using parallel springs of this configuration, the base body and the driven link are connected to four members, that is, the first link, the second link, the first leaf spring and the second leaf spring to constitute an annular chain in link mechanism. This chain is connected as a rotation pair by four pins, that is, the first base end pin, the second base end pin, the first tip pin, and the second tip pin. Thus, the two-degree-of-freedom rotation mechanism using parallel springs is lightweight, has a small number of parts and a simple structure, and is made at a low cost. It is excellent in sterilizing and disinfecting property because it has a small number of parts and a simple structure. Moreover, since the chain includes the first leaf spring and the second leaf spring as elements, excessive load is not applied to a target. The two-degree-of-freedom rotation mechanism using parallel springs can be operated by being incorporated into an apparatus such as a manipulator, or by being directly mounted on a forearm or the like of a human body. By using the two-degree-of-freedom rotation mechanism using parallel springs in the manipulator or the forearm, it is possible to convert independent parallel and linear motions of a pair of the first link and the second link into the two-degree-of-freedom operation of the driven link and take out by deforming the first leaf spring and the second leaf spring. As a result, for example, precise probe scanning in a space-saving manner and motion support operation of a forearm that is ahead of a wrist joint are realized.

The present invention provides the two-degree-of-freedom rotation mechanism using parallel springs, further including: a first support rod including a base end fixed to the base body and extending along the first link and the first leaf spring; a second support rod including a base end fixed to the base body and extending along the second link and the second leaf spring; a pitch shaft including both ends supported by tips of the first support rod and the second support rod; a rocking disk in which a direction parallel to a diameter of the rocking disk is rotatably supported along the pitch shaft; a yaw shaft which is rotatably supported on the rocking disk in a vertical direction; and a holder which is fixed to one end of the yaw shaft and is rotatable regarding the rocking disk, in which the driven link is a rotating disk fixed to the other end of the yaw shaft and rotatable regarding the rocking disk.

According to the two-degree-of-freedom rotation mechanism using parallel springs of this configuration, a pair of first support rod and second support rod are protruded from the base body and fixed in parallel. The first support rod and the second support rod are disposed along the first link and the first leaf spring, and the second link and the second leaf spring, respectively. The pitch shaft is supported by the first support rod and the second support rod over the tips. By the pitch shaft, the rocking disk is rotatably supported. The yaw shaft freely rotatable about the center is vertically supported on the rocking disk. On the yaw shaft, the holder is fixed to one end and the rotating disk is fixed to the other end. The tips of the first leaf spring and the second leaf spring are connected to the rotating disk as a rotation pair by the first tip pin and the second tip pin with the rotation center interposed therebetween. When the first link and the second link advance, the rotating disk rotates forward through the pitch shaft integrally with the rocking disk. Therefore, the holder also rotates forward. In this specification, forward rotation and backward rotation of the driven link are referred to as forward rotation and backward rotation in the case of a manipulator, and are referred to as palmar flexion and dorsiflexion in the case of a forearm motion support device. When the first link and the second link retract, the rotating disk rotates backward through the pitch shaft integrally with the rocking disk. Therefore, the holder also rotates backward. When making difference (moving with difference) in the advance and retreat amounts of the first link and the second link, the rotating disk rotates clockwise or counterclockwise about the yaw shaft. Therefore, the holder also rotates clockwise or counterclockwise. The first link and the second link can be moved with difference while advancing or retracting. In this case, the holder can operate, for example, an ultrasonic probe held by the holder, to stroke the target while applying contact pressure.

The present invention provides the two-degree-of-freedom rotation mechanism using parallel springs in which the first leaf spring and the second leaf spring are provided with J-shaped tip bent portions bent in a direction in which the tips thereof approach each other.

According to the two-degree-of-freedom rotation mechanism using parallel springs of this configuration, when the rotating disk rotates at 90° around the yaw shaft, contact between the first leaf spring and the second leaf spring can be avoided. When the yaw shaft rotation angle is 90° and an interference avoidance distance from the first tip pin or the second tip pin (tip passive joint) to the counterpart spring is larger than a spring width, contact between the first leaf spring and the second leaf spring can be avoided. By forming the J-shaped tip bent portion at the tips of the first leaf spring and the second leaf spring, the interference avoidance distance can be secured without being restricted by the spring width.

The present invention provides the two-degree-of-freedom rotation mechanism using parallel springs in which the first leaf spring and the second leaf spring have a smaller spaced distance between the tips than a spaced distance between the base ends.

According to the two-degree-of-freedom rotation mechanism using parallel springs of this configuration, when a line passing through the first base end pin and the second base end pin and a line passing through the first tip pin and the second tip pin are parallel to each other on the same plane, the spaced distance between the first tip pin and the second tip pin is smaller than the spaced distance between the first base end pin and the second base end pin. That is, the first leaf spring and the second leaf spring have a smaller spaced distance between the tips than the spaced distance between the base ends. Thus, the first leaf spring and the second leaf spring can rotate the rotating disk at a large rotation angle in a smaller linear movement distance of the first link and the second link, as compared to when the spaced distance between tips is larger than the spaced distance between the base ends. Further, the rotating disk and the rocking disk can be made compact by forming the disk small in the radial direction.

The present invention provides the two-degree-of-freedom rotation mechanism using parallel springs in which the holder detachably holds an ultrasonic probe.

According to the two-degree-of-freedom rotation mechanism using parallel springs of this configuration, the ultrasonic probe is mounted on the holder. In other words, the two-degree-of-freedom rotation mechanism using parallel springs can be used as a manipulator for intra-operative laparoscopic ultrasonic diagnosis. The ultrasonic probe mounted on the holder can rotate with two-degree-of-freedom about the pitch shaft and the yaw shaft by independent linear operations of the first link and the second link. The ultrasonic probe can acquire internal information of the target in real time by scanning along the surface of the target by the two-degree-of-freedom rotation. Particularly, according to the manipulator using the two-degree-of-freedom rotation mechanism using parallel springs, it is possible to perform a rotation operation around the contact point of the target (operation to stroke the target surface) while realizing a compact tip shape, so ideal probe scanning is realized. The manipulator can absorb reaction force from the target by the elasticity of the first leaf spring and the second leaf spring, and make it possible to contact the ultrasonic probe with an appropriate force to the target without giving an excessive load.

The present invention provides the two-degree-of-freedom rotation mechanism using parallel springs in which the first leaf spring and the second leaf spring are made of a nickel titanium alloy.

According to the two-degree-of-freedom rotation mechanism using parallel springs of this configuration, the nickel titanium alloy is used for the first leaf spring and the second leaf spring. The nickel titanium alloy is biocompatible and has a superelastic property. Therefore, according to a manipulator for intra-operative laparoscopic ultrasonic diagnosis using the two-degree-of-freedom rotation mechanism using parallel springs, while maintaining biocompatibility, it is possible to satisfy the rotation operation range 20° to 90° around the pitch shaft and the rotation operation range of ±90° around the yaw shaft required for ultrasonic diagnosis.

The present invention provides the two-degree-of-freedom rotation mechanism using parallel springs in which the first link and the second link are parallel.

According to the two-degree-of-freedom rotation mechanism using parallel springs of this configuration, the long first link and the long second link can be disposed without interfering with each other. When the two-degree-of-freedom rotation mechanism using parallel springs is used in a manipulator for intra-operative laparoscopic ultrasonic diagnosis, the first link and the second link are accommodated in an outer cylinder. The outer cylinder is inserted through a trocar that has passed through an incision of an abdomen. Therefore, it is necessary for the manipulator to secure a distance (outer cylinder length) from the tip to the manipulator drive unit located outside within a predetermined length. By disposing the first link and the second link in parallel, it is easy to secure the outer cylinder length while avoiding mutual interference.

The present invention provides the two-degree-of-freedom rotation mechanism using parallel springs in which the base body is attached and fixed to a peripheral portion of a joint of a human body, and the driven link is attached and fixed between a first portion of the peripheral portion and a second portion of the peripheral portion.

According to the two-degree-of-freedom rotation mechanism using parallel springs of this configuration, the base body is attached on the peripheral portion of the joint of the human body, and the driven link is attached to sandwich two peripheral portions of the joint. When the first link and the second link advance, the peripheral portion of the joint bends forward through the joint. When the first link and the second link retract, the peripheral portion of the joint is dorsiflexed through the joint. When making difference (moving with difference) in the advance and retreat amounts of the first link and the second link, the peripheral portion of the joint is abducted or adducted. The first link and the second link can be moved with difference while advancing or retracting. In this case, the peripheral portion of the joint can be operated to stroke the target while applying contact pressure. That is, the two-degree-of-freedom rotation mechanism using parallel springs can be applied to a support device that performs a support operation for smoothly moving the peripheral portion of the joint of the human body. Since a support device using the two-degree-of-freedom rotation mechanism using parallel springs includes the first leaf spring and the second leaf spring in the chain, the reaction force received from the driven link is absorbed by the deformation of the first leaf spring and the second leaf spring, and it is possible to prevent application of an excessive load to the joint of the human body.

The present invention provides a two-degree-of-freedom rotation mechanism with parallel springs, in which the peripheral portion of the joint of the human body is a forearm, and the first portion is a wrist, and the second portion is a base of fingers.

According to the two-degree-of-freedom rotation mechanism using parallel springs of this configuration, the base body is attached to the forearm, and the driven link is attached to the back of the hand or the like. When the first link and the second link advance, the hand is palm-flexed through the wrist. When the first link and the second link retract, the hand is dorsiflexed through the wrist. When making difference (moving with difference) in the advance and retreat amounts of the first link and the second link, the hand is abducted or adducted. The first link and the second link can be moved with difference while advancing or retracting. In this case, the palm can be operated to stroke the target while applying contact pressure. That is, the two-degree-of-freedom rotation mechanism using parallel springs can be used as a forearm motion support device for performing a forearm motion support operation. In a forearm motion support device using the two-degree-of-freedom rotation mechanism using parallel springs, since the first leaf spring and the second leaf spring are included in the chain, the reaction force received from the driven link is absorbed by the deformation of the first leaf spring and the second leaf spring, and it is possible to prevent application of an excessive load to the wrist joint.

Advantageous Effects of Invention

According to the present invention, it is lightweight, has a small number of parts and a simple structure, is capable of operating a driven link with two-degree-of-freedom at low cost, is excellent in sterilizing and disinfecting property, and does not apply excessive burden to a target.

DETAILED DESCRIPTION OF THE PREFERRED EMBODIMENTS

Hereinafter, respective embodiments which specifically disclose a two-degree-of-freedom rotation mechanism using parallel springs according to the present invention will be described in detail, with reference to appropriate drawings. However, a detailed description more than necessary may be omitted. For example, detailed descriptions of already well-known matters and duplicate descriptions of substantially identical components may be omitted in some cases. This is to avoid unnecessary redundancy of the following description and to facilitate understanding by those skilled in the art. The accompanying drawings and the following description are provided to enable those skilled in the art to fully understand the present disclosure, and are not intended to limit the subject matter described in the claims. In the following embodiments, a manipulator according to the present invention will be described by exemplifying a manipulator used for laparoscopic surgery in a minimally invasive surgical technique, for example.

First Embodiment

Figure 1:
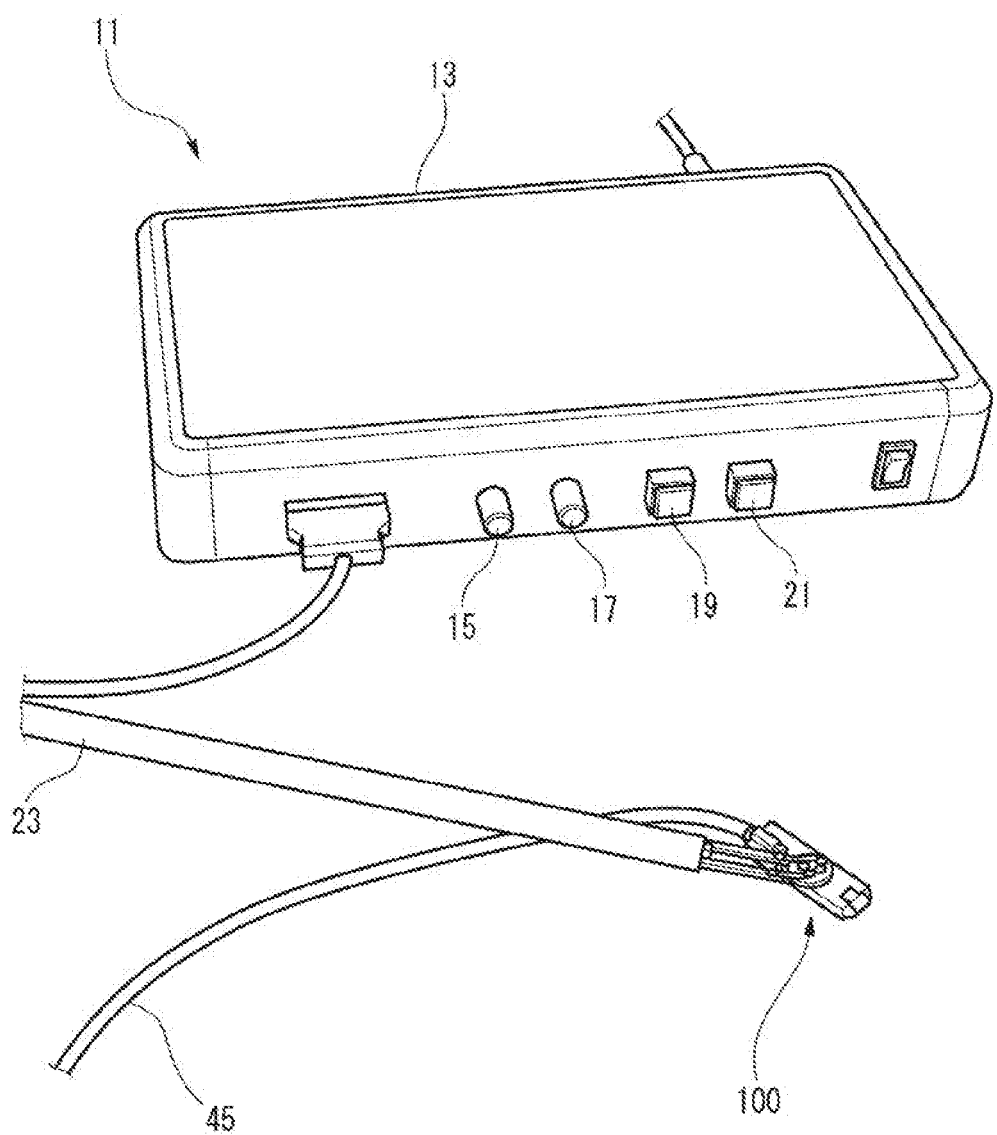
FIG. 1 is a configuration diagram of a manipulator device unit according to a first embodiment.

In a first embodiment, as an apparatus to which a two-degree-of-freedom rotation mechanism using parallel springs according to the present invention is applied, for example, a manipulator for intra-operative laparoscopic ultrasonic diagnosis will be described as an example. FIG. 1 is a configuration diagram of a manipulator device unit according to the first embodiment.

A manipulator 100 is attached to a manipulator device unit 11. The manipulator device unit 11 includes a control unit 13 and a manipulator drive unit (not illustrated). The control unit 13 is provided with a pitch rotation speed adjustment knob 15, a yaw rotation speed adjustment knob 17, a pitch-0-degree yaw-0-degree posture switch (initial posture switch 19), and a pitch-20-degree yaw-0-degree posture switch (pitch inclination posture switch 21).

In the manipulator drive unit, a pair of linear motion motors (not illustrated) are provided in a unit body portion (not illustrated) including a grip portion. A pitch button (not illustrated) and a yaw button (not illustrated) for respectively pitch-driving and yaw-driving the manipulator 100 while grasping the grip portion are disposed on the grip portion of the unit body portion. The linear motion motor is rotationally controlled independently by the control unit 13. The base end of an outer cylinder 23 is fixed to the unit body portion.

Figure 2:
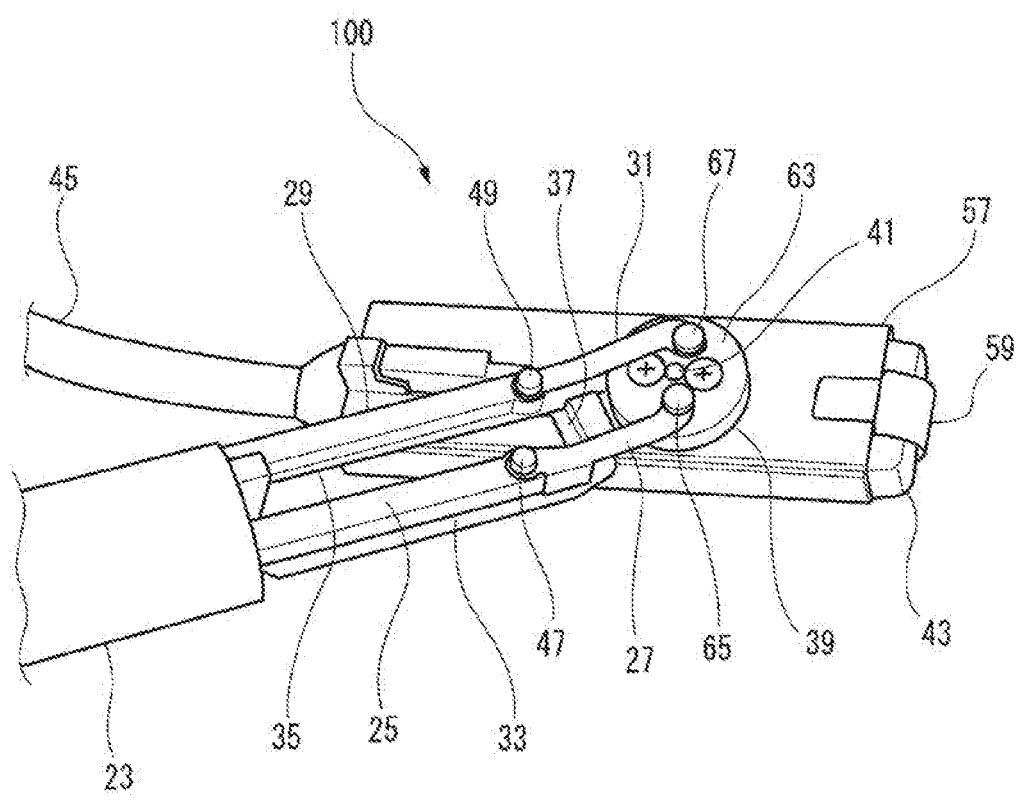
FIG. 2 is an enlarged view of the manipulator illustrated in FIG. 1.

FIG. 2 is an enlarged view of the manipulator illustrated in FIG. 1. The manipulator 100 is attached to the tip of the outer cylinder 23 extending from the manipulator drive unit. The manipulator 100 includes a base body, a first link 25, a first leaf spring 27, a second link 29, a second leaf spring 31, and a driven link. The manipulator 100 further includes a first support rod 33, a second support rod 35, a pitch shaft 37, a rocking disk 39, a yaw shaft 41, and a holder. In the manipulator 100, the base body is the above-described unit body portion.

Figure 3:
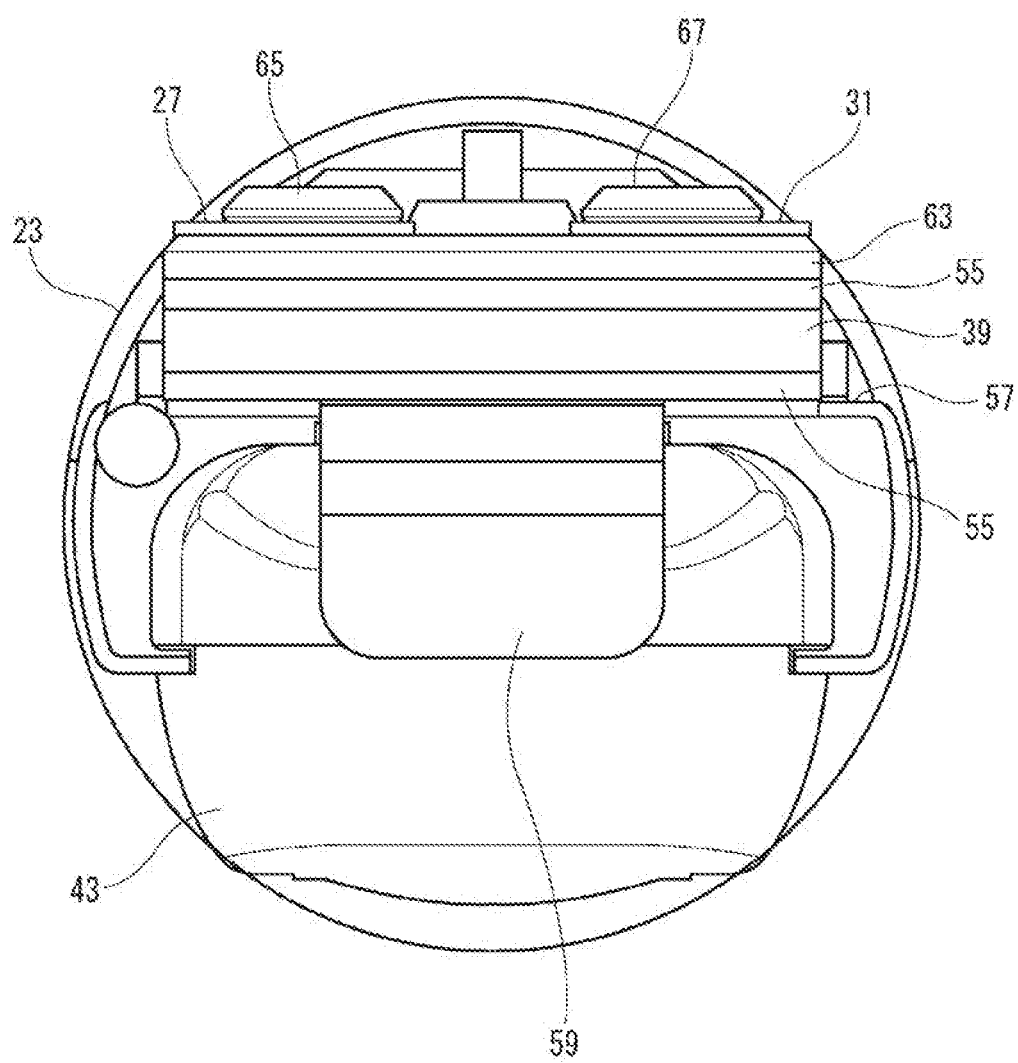
FIG. 3 is a front view of the manipulator.

FIG. 3 is a front view of the manipulator. The outer cylinder 23 is formed in a circular shape. A part of the outer cylinder 23 has a half-moon shape, and a short pipe of the same half-moon shape is attached thereto. Linear bearings are installed inside the short pipe. The linear bearings support the movement of a cable 45 and prevent the pneumoperitoneum gas from leaking, by passing through the cable 45 of an ultrasonic probe 43 mounted on the holder.

In the front view, the manipulator 100 is disposed radially inward of the outer cylinder 23 without an outer shape thereof protruding from the outer cylinder 23. For example, in standard laparoscopic surgery, the manipulator 100 is inserted through a trocar that has passed through a small (approximately ½ inch) incision in an abdomen. A surgeon manipulates the manipulator 100 disposed at a diagnosis site inside from outside of the abdomen through the trocar.

Figure 4:
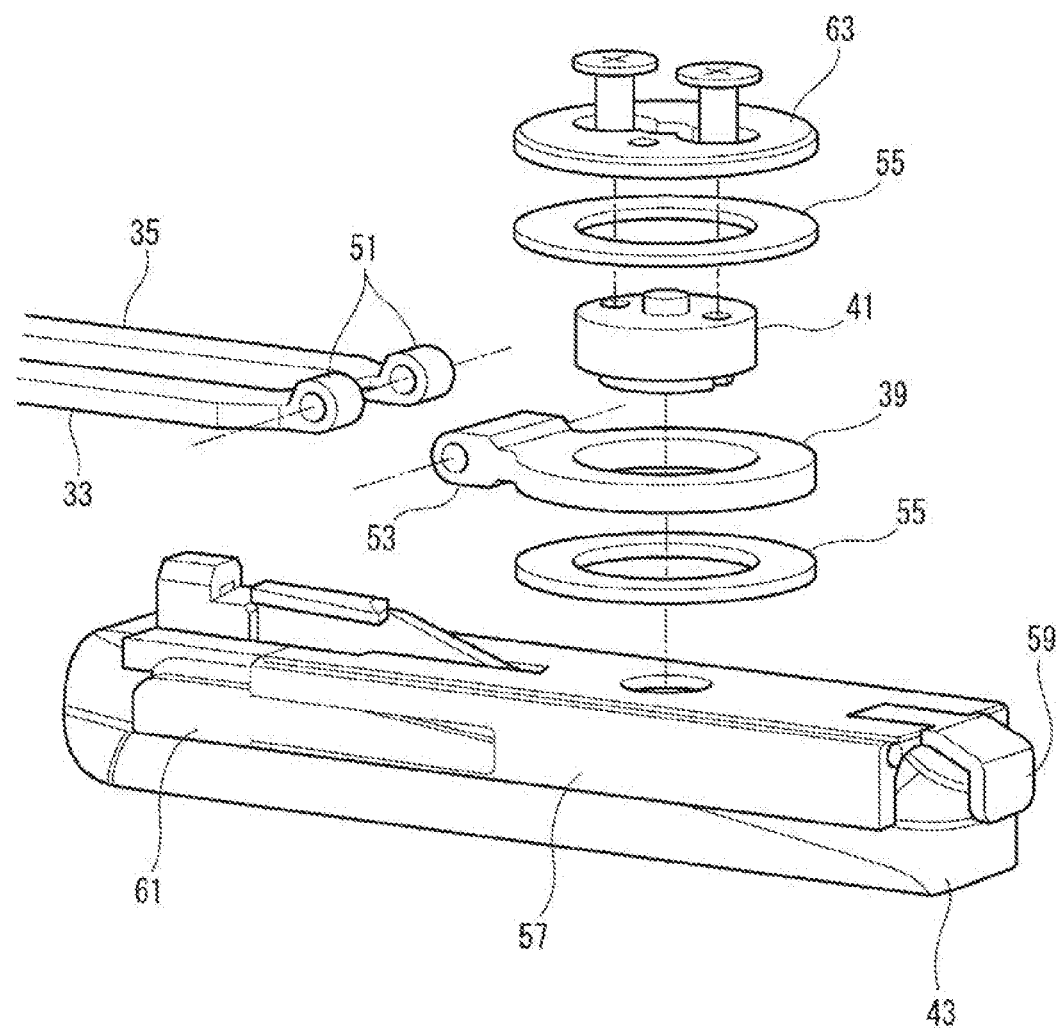
FIG. 4 is an exploded perspective view of the manipulator illustrated in FIG. 3.
Figure 4:
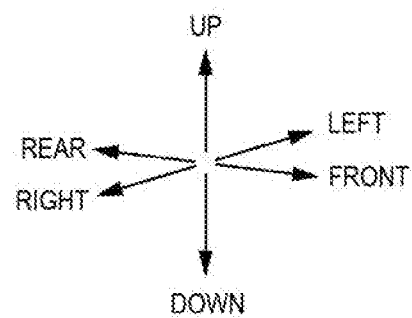

FIG. 4 is an exploded perspective view of the manipulator illustrated in FIG. 3. In the present embodiment, the directions of the up, down, front, rear, right, and left follow directions of the arrows illustrated in FIG. 4.

The first link 25 is capable of advancing and retracting in the longitudinal direction of first link 25 with respect to the unit body portion by one linear motion motor of the manipulator drive unit. A rotational motion of the linear motion motor is, for example, converted into linear motion by a ball screw mechanism and transmitted to the first link 25.

The first leaf spring 27 is formed in, for example, a rectangular shape. The longitudinal base end of the first leaf spring 27 is connected to the tip of the first link 25 as a rotation pair by a first base end pin 47. The first base end pin 47 passes through the longitudinal base end of the first leaf spring 27 in the thickness direction.

The second link 29 is disposed with the first link 25 side by side. The second link 29 is capable of advancing and retracting in the longitudinal direction of second link 29 with respect to the unit body portion by the other linear motion motor of the manipulator drive unit. A rotational motion of the linear motion motor is, for example, converted into linear motion by a ball screw mechanism and transmitted to the second link 29.

The second leaf spring 31 is formed in the same rectangular shape as the first leaf spring 27. The longitudinal base end of the second leaf spring 31 is connected to the tip of the second link 29 as a rotation pair by a second base end pin 49 in the same direction as the first base end pin 47. The second base end pin 49 passes through the longitudinal base end of the second leaf spring 31 in the thickness direction.

In the present embodiment, the first link 25 and the second link 29 of the manipulator 100 are parallel to each other. The first link 25 and the second link 29 parallel to each other are inserted inwardly of the outer cylinder 23 so as to freely linearly move independently.

The base end of the first support rod 33 is fixed to the unit body portion. The first support rod 33 extends along the first link 25 and the first leaf spring 27.

The base end of the second support rod 35 is fixed to the unit body portion. The second support rod 35 extends along the second link 29 and the second leaf spring 31.

Pitch shaft bearings 51 are respectively formed at the tips of the first support rod 33 and the second support rod 35.

Both left and right ends of the pitch shaft 37 are supported by the pitch shaft bearings 51 of the tips of both of the first support rod 33 and the second support rod 35. The pitch shaft 37 may be fixedly supported or may be rotatably supported by the pitch shaft bearing 51.

The rocking disk 39 is formed in an annular shape. A direction parallel to the diameter of the rocking disk 39 is rotatably supported along the pitch shaft 37. In the present embodiment, a pitch shaft insertion portion 53 in the string direction is formed on the rocking disk 39. The pitch shaft 37 with both ends supported by the pitch shaft bearing 51 is inserted through the pitch shaft insertion portion 53. As a result, the rocking disk 39 is freely swingable around the pitch shaft at the tips of a pair of first support rod 33 and second support rod 35.

The yaw shaft 41 is rotatably supported on the rocking disk 39 in the vertical direction. In the present embodiment, the yaw shaft 41 is rotatably fitted into the inner hole of the rocking disk 39. The manipulator 100 can be easily attached to and detached from the first link 25, the second link 29, and the tips of the first support rod 33 and the second support rod 35 by unscrewing the first base end pin 47, the second base end pin 49 and the yaw shaft 41.

The holder is fixed to one end of the yaw shaft 41 and is rotatable regarding the rocking disk 39. The holder is fixed to a cross section on the one end side (lower end side) of the yaw shaft 41 by a pair of screws. An annular plain bearing 55 for friction reduction is interposed between the holder and the rocking disk 39. The holder detachably holds the ultrasonic probe 43. That is, in the manipulator 100 of the present embodiment, the holder is an ultrasonic probe holder 57.

The upper surface of the ultrasonic probe holder 57 is fixed to the yaw shaft 41. A probe locking claw 59 is provided at the tip of the ultrasonic probe holder 57. At the rear end of the ultrasonic probe holder 57, a slider 61 is provided to be slidable in the front and rear direction. When the slider 61 is retracted, the ultrasonic probe holder 57 locks the tip of the ultrasonic probe 43 to the probe locking claw 59, and the rear end of the ultrasonic probe 43 is locked by the slider 61 slid forward, so it can be easily mounted.

In the manipulator 100, the driven link is a rotating disk 63. The rotating disk 63 is fixed to the other end of the yaw shaft 41 and is rotatable regarding the rocking disk 39. The rotating disk 63 is fixed to a cross section on the other end side (upper end side) of the yaw shaft 41 by a pair of screws. The annular plain bearing 55 for friction reduction is interposed between the rotating disk 63 and the rocking disk 39.

On the yaw shaft 41 and the rotating disk 63, a first tip pin 65 and a second tip pin 67 are supported on both sides sandwiching the rotation center. The first leaf spring 27 and the second leaf spring 31 are connected to the yaw shaft 41 and the rotating disk 63 as a rotation pair through the first tip pin 65 and the second tip pin 67.

In the manipulator 100, the outer cylinder 23 has a total length of 370 mm and a diameter of 15 mm, and the ultrasonic probe 43 (for example, L43K, Hitachi Aloka Medical Ltd., Japan) with a diameter of about 12 mm can be mounted on the tip.

Figure 5:
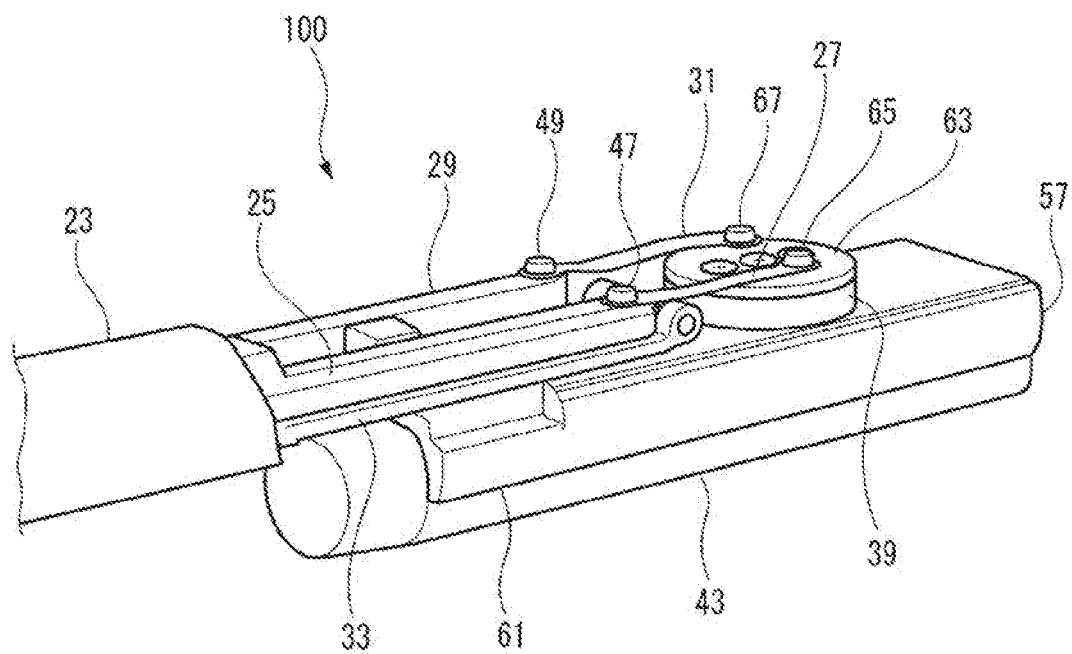
FIG. 5 is a perspective view of the manipulator in a non-operating state.

FIG. 5 is a perspective view of the manipulator in a non-operating state. The manipulator 100 becomes an initial posture by the pitch inclination posture switch 21. In the initial posture, the first base end pin 47 and the second base end pin 49 are in the same advancing and retracting position, and the ultrasonic probe 43 is disposed in parallel to the first support rod 33 and the second support rod 35.

Figure 6:
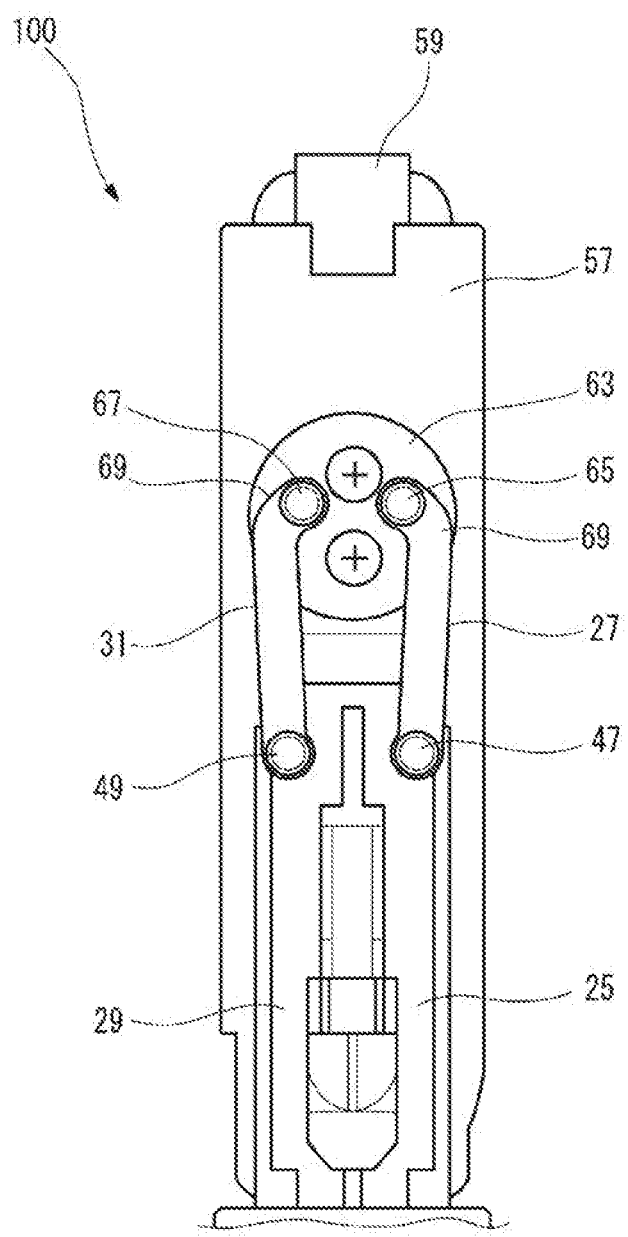
FIG. 6 is a schematic diagram of the manipulator in a non-operating state in a plan view.

FIG. 6 is a schematic diagram of the manipulator in a non-operating state in a plan view. In the initial posture, the first leaf spring 27 and the second leaf spring 31 have a smaller spaced distance between the tips than the spaced distance between the base ends.

Figure 7:
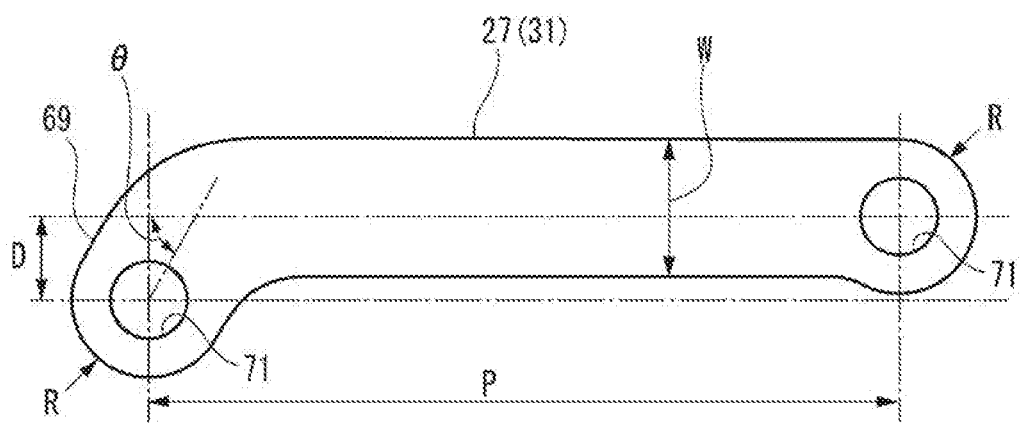
FIG. 7 is a plan view of the first leaf spring.

FIG. 7 is a plan view of the first leaf spring. The first leaf spring 27 and the second leaf spring 31 are provided with J-shaped tip bent portions 69 bent in a direction in which the tips thereof approach each other. Specifically, the first leaf spring 27 and the second leaf spring 31 are formed such that a pitch length P of the pin hole 71 is 13.5 mm, a plate width W is 2.5 mm, an interval D from the shaft to the pin hole 71 of the tip bent portion 69 is 1.5 mm, a chamfer radius R of both ends is 1.8 mm, and a J-shaped bending angle $\theta$ is about 60°.

The first leaf spring 27 and the second leaf spring 31 are formed using a nickel titanium alloy, for example. The first leaf spring 27 and the second leaf spring 31 are formed with a thickness of about 0.2 mm. By using a nickel titanium alloy with a plate thickness of 0.2 mm, the manipulator 100 achieves an operation range of pitch rotation of 20° to 90° and an operation range ±90° of yaw rotation required for ideal ultrasonic diagnosis.

Figure 8:
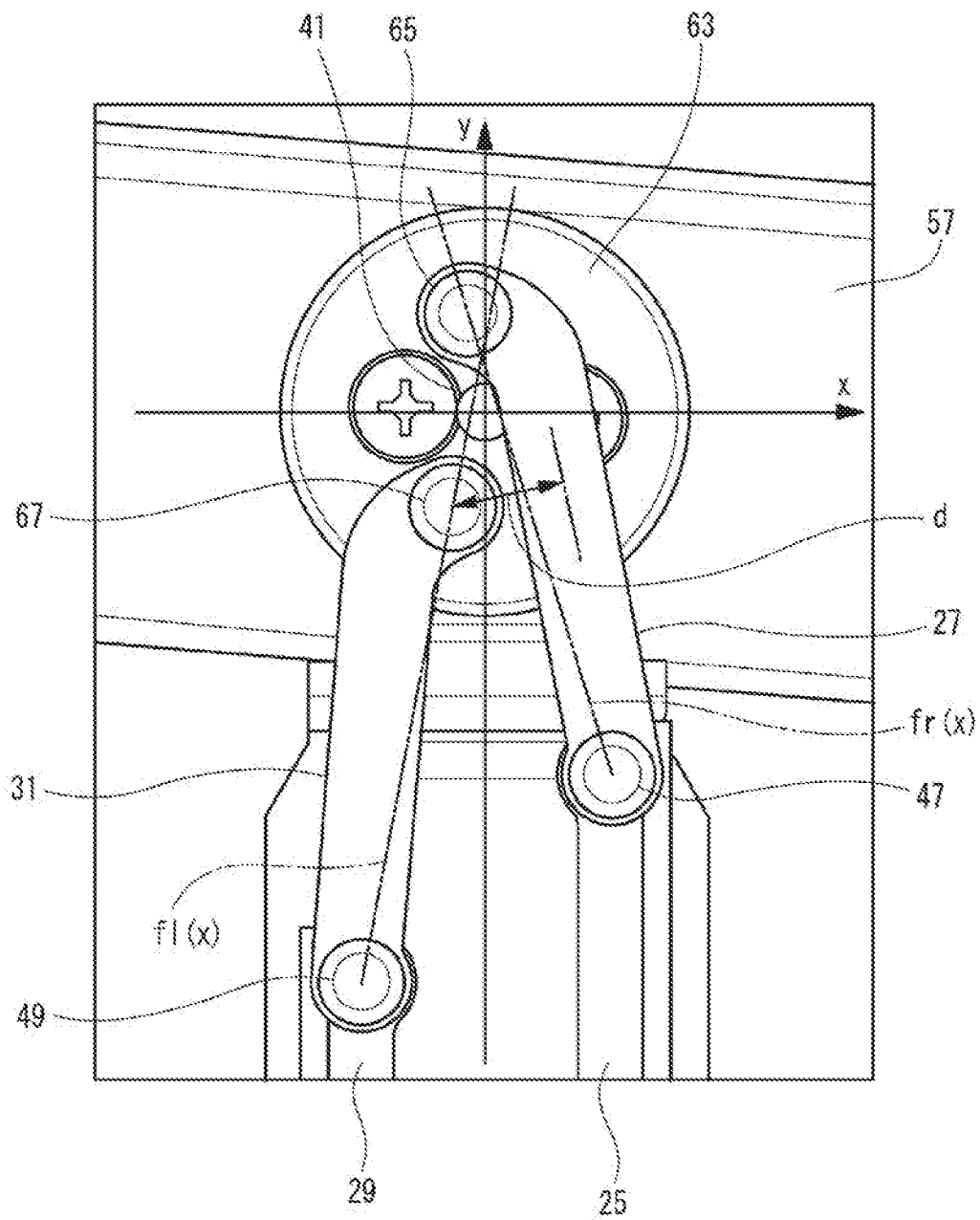
FIG. 8 is a schematic diagram for explaining spring contact avoidance and singularity avoidance during yaw shaft rotation.

FIG. 8 is a schematic diagram for explaining spring contact avoidance and singularity avoidance during yaw shaft rotation. For example, singularity in a robot such as the manipulator 100 according to the present embodiment means a position or posture in which one or more degrees of freedom degenerate, and the robot (for example, the manipulator 100) becomes inoperative. More specifically, to operate a robot (for example, the manipulator 100), it is necessary to transpose the mechanism arrangement with a mathematical expression and determine how to move the linear motion motor how much to the target position. However, singularity means that the mathematical expression cannot be solved. For example, a state in which the joints respectively corresponding to the base end and tip of the first leaf spring 27 and the tip of the second leaf spring 31 are aligned on a straight line is singularity.

To determine the shapes of the first leaf spring 27 and the second leaf spring 31, three conditions need to be satisfied. A first condition is spring contact avoidance when the yaw shaft is rotated by 90°. Therefore, in the manipulator 100, when the yaw shaft is rotated by 90°, a distance d between the center of the first tip pin 65 or the second tip pin 67 and the shaft of the adjacent first link 25 or second link 29 is set larger than the plate width W (d>W).

A second condition is singularity avoidance when the yaw shaft is rotated by 90°. Therefore, in the manipulator 100, when the yaw shaft is rotated by 90°, the straight line fr(x) connecting the first base end pin 47 and the first tip pin 65 and the straight line fl(x) connecting the second base end pin 49 and the second tip pin 67 are set to satisfy fr(0)>0 and fl(0)>0.

Figure 9:
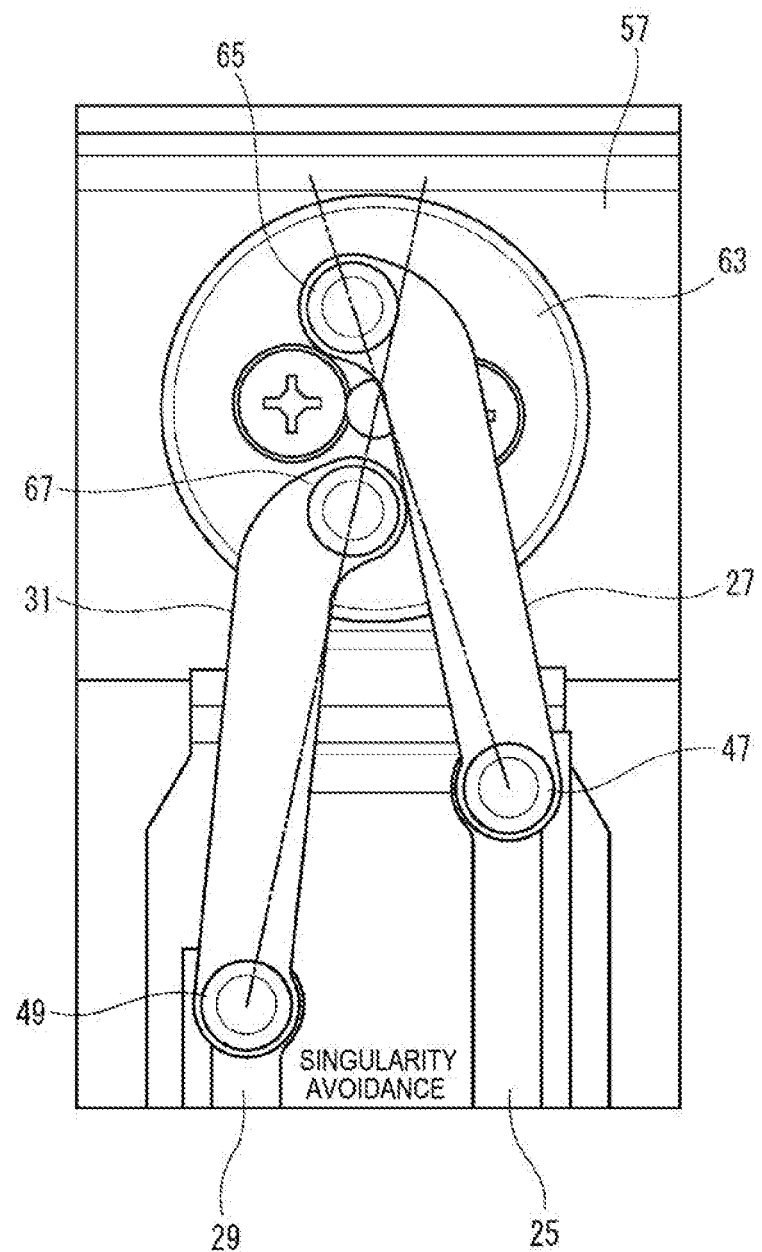
FIG. 9 is an operation explanatory diagram for explaining singularity avoidance when the yaw shaft is rotated by 90°.

FIG. 9 is an operation explanatory diagram for explaining singularity avoidance when the yaw shaft is rotated by 90°. Thus, the manipulator 100 can avoid the singularity when the yaw shaft is rotated by 90°.

Figure 10:
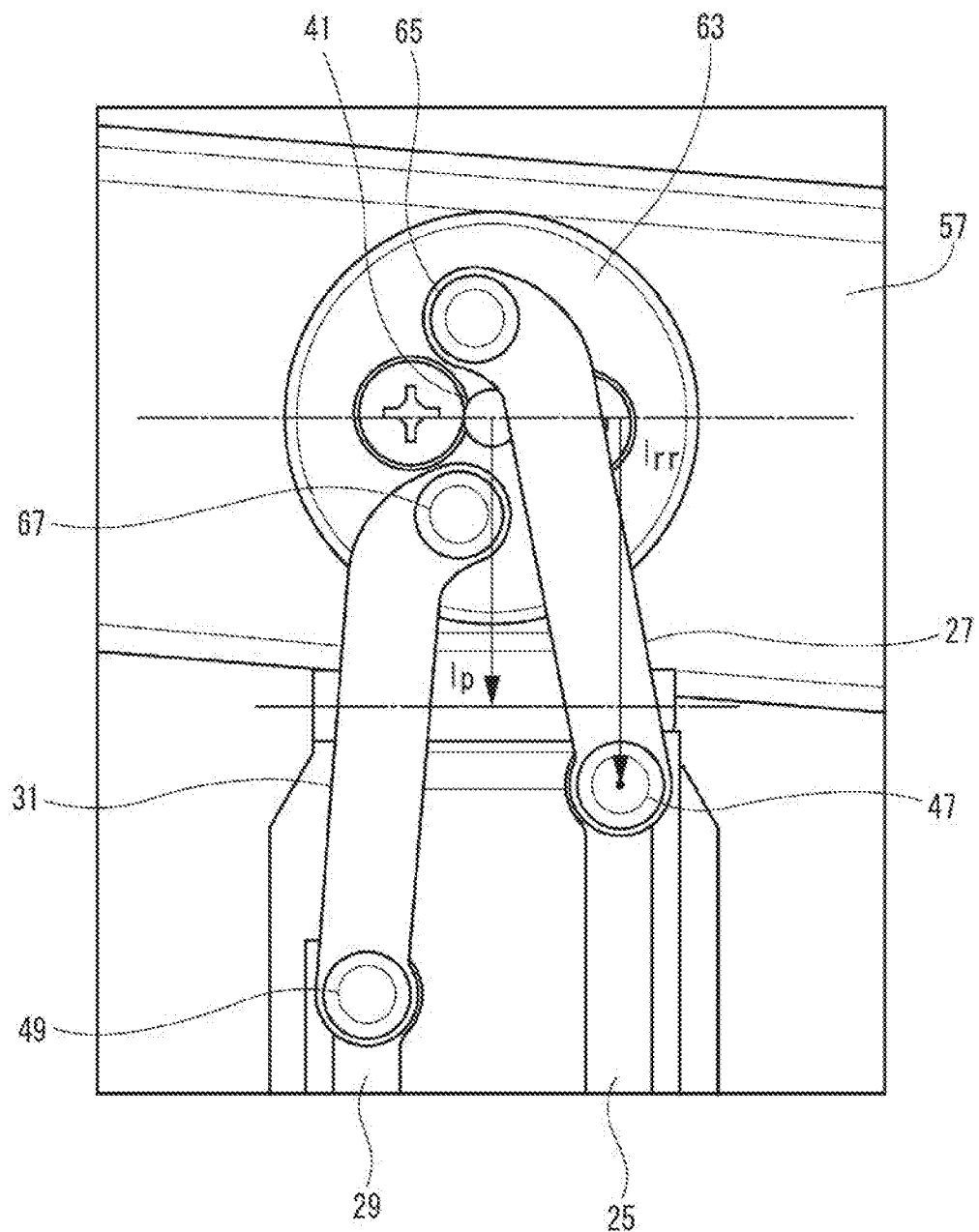
FIG. 10 is a schematic diagram for explaining pitch shaft interference avoidance during yaw shaft rotation.

FIG. 10 is a schematic diagram for explaining pitch shaft interference avoidance during yaw shaft rotation. A third condition is interference avoidance with the pitch shaft 37 when the yaw shaft is rotated by 90°. Therefore, in the manipulator 100, when the yaw shaft is rotated by 90°, a distance lrr from the yaw shaft 41 to a closer one of the first tip pin 65 or the second tip pin 67 is set to be larger than a distance lp from the yaw shaft 41 to the pitch shaft 37 (lrr>lp).

Figure 11:
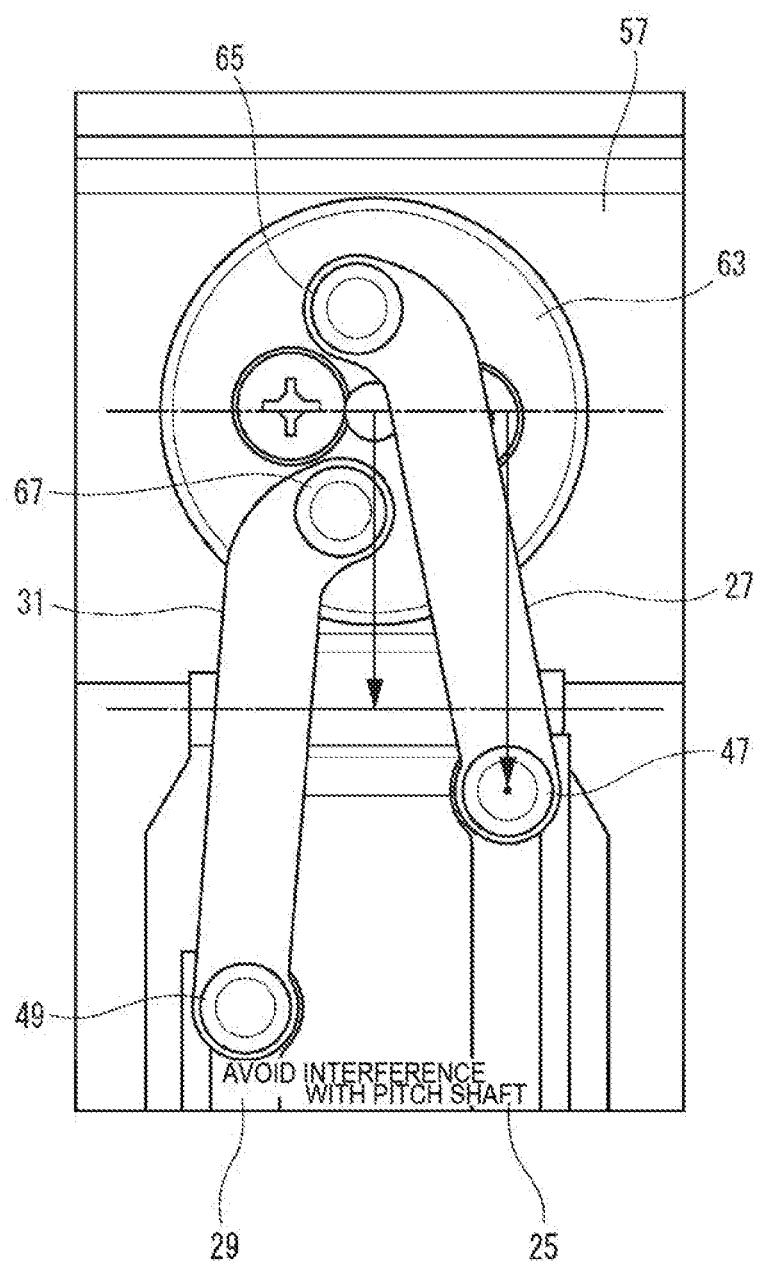
FIG. 11 is an operation explanatory diagram for explaining pitch shaft interference avoidance when the yaw shaft is rotated by 90°.

FIG. 11 is an operation explanatory diagram for explaining pitch shaft interference avoidance when the yaw shaft is rotated by 90°. Thus, the manipulator 100 can avoid interference with the pitch shaft 37 when the yaw shaft is rotated by 90°. The shapes of the first leaf spring 27 and the second leaf spring 31 that satisfy the first condition to the third condition are as illustrated in FIG. 7.

Next, the operation of the above configuration will be described.

In the two-degree-of-freedom rotation mechanism using parallel springs of the basic configuration according to the present embodiment, the base body and the driven link are connected to four members, that is, the first link 25, the second link 29, the first leaf spring 27 and the second leaf spring 31 to constitute an annular chain in link mechanism. This chain is connected as a rotation pair by four pins, that is, the first base end pin 47, the second base end pin 49, the first tip pin 65 and the second tip pin 67. Thus, the two-degree-of-freedom rotation mechanism using parallel springs is lightweight, has a small number of parts and a simple structure, and is made at a low cost.

As the two-degree-of-freedom rotation mechanism using parallel springs has a simple structure with a small number of components, it is excellent in sterilizing and disinfecting property. Moreover, since the chain includes the first leaf spring 27 and the second leaf spring 31 as elements, excessive load is not applied to a target.

The two-degree-of-freedom rotation mechanism using parallel springs can be operated by being incorporated into an apparatus such as a manipulator 100, or by being directly mounted on a forearm or the like of a human body. By using the two-degree-of-freedom rotation mechanism using parallel springs in the manipulator 100 or the forearm, independent parallel and linear motions of a pair of the first link 25 and the second link 29 can be converted into the two-degree-of-freedom operation of the driven link and taken out by deforming the first leaf spring 27 and the second leaf spring 31. As a result, for example, precise probe scanning in a space-saving manner and motion support operation of a forearm that is ahead of a wrist joint are realized.

In the manipulator 100 of the above-described configuration example, a pair of first support rods 33 and second support rod 35 are protruded and fixed in parallel from the unit body portion that is the base body. The first support rod 33 and the second support rod 35 are disposed along the first link 25 and the first leaf spring 27, and the second link 29 and the second leaf spring 31, respectively. The pitch shaft 37 is supported by the first support rod 33 and the second support rod 35 over the tips. By the pitch shaft 37, the rocking disk 39 is rotatably supported. The yaw shaft 41 freely rotatable about the center is vertically supported on the rocking disk 39. On the yaw shaft 41, the holder is fixed to one end and the rotating disk 63 is fixed to the other end. The tips of the first leaf spring 27 and the second leaf spring 31 are connected to the rotating disk 63 as a rotation pair by the first tip pin 65 and the second tip pin 67 with the rotation center interposed therebetween.

Figure 12:
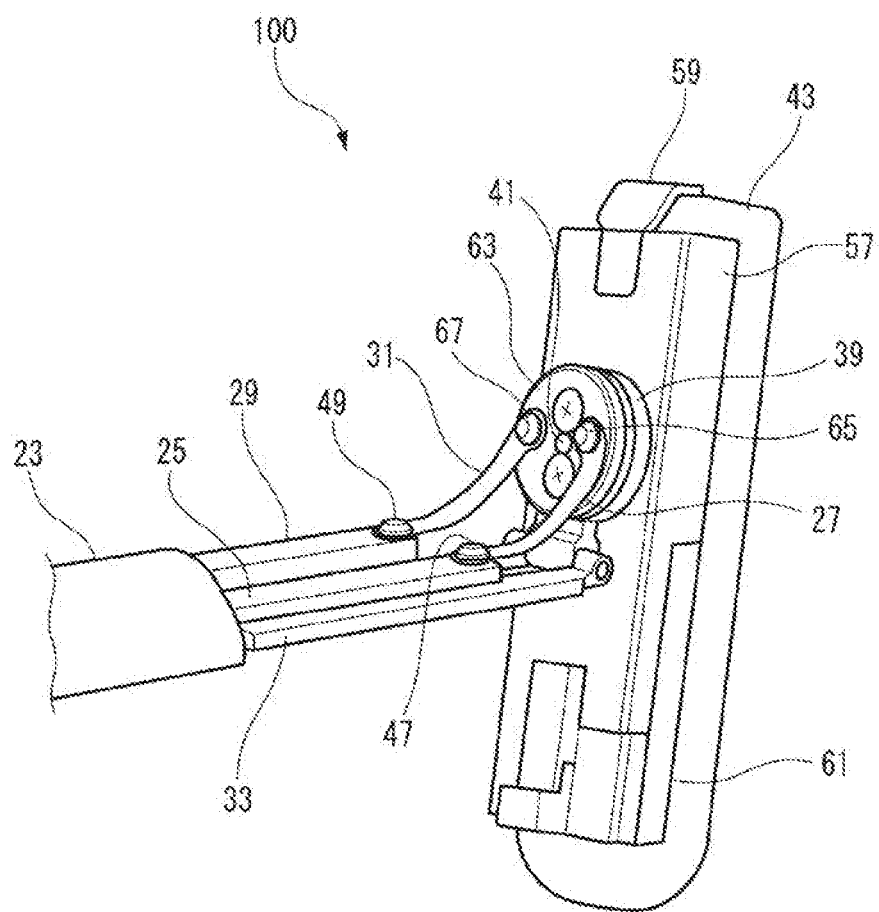
FIG. 12 is a perspective view of the manipulator during backward rotation.

FIG. 12 is a perspective view of the manipulator during backward rotation. When the first link 25 and the second link 29 advance, the rotating disk 63 rotates forward through the pitch shaft 37 integrally with the rocking disk 39. Therefore, the holder also rotates forward. In this specification, forward rotation and backward rotation of the driven link are referred to as forward rotation and backward rotation in the case of the manipulator 100, and are referred to as palmar flexion and dorsiflexion in the case of a forearm motion support device to be described later. When the first link 25 and the second link 29 retract, the rotating disk 63 rotates backward through the pitch shaft 37 integrally with the rocking disk 39. Therefore, the holder also rotates backward.

Figure 13:
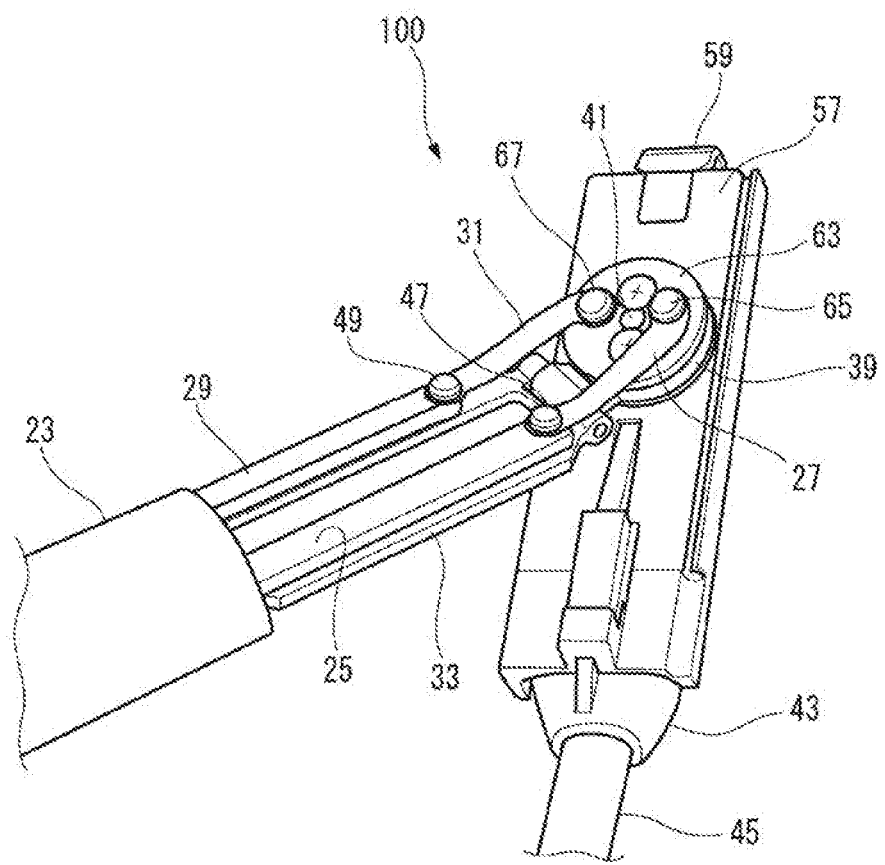
FIG. 13 is a perspective view of the manipulator during backward leftward rotation.

FIG. 13 is a perspective view of the manipulator during backward leftward rotation. When making difference (moving with difference) in the advance and retreat amounts of the first link 25 and the second link 29, the rotating disk 63 rotates clockwise or counterclockwise about the yaw shaft 41. Therefore, the holder also rotates clockwise or counterclockwise. The first link 25 and the second link 29 can be moved with difference while advancing or retracting. In this case, the holder can operate the ultrasonic probe 43 held by the holder to stroke the target while applying contact pressure.

It is to be noted that the ultrasonic probe 43 is provided with a projection for holding with forceps. When yaw rotation is performed, it is necessary to first perform pitch rotation at 20° to avoid interference by the projection. The posture is performed by the pitch inclination posture switch 21.

In the manipulator 100, when the rotating disk 63 rotates at 90° around the yaw shaft 41, contact between the first leaf spring 27 and the second leaf spring 31 can be avoided. When the yaw shaft rotation angle is 90° and an interference avoidance distance from the first tip pin 65 or the second tip pin 67 to the counterpart spring is larger than a spring width, contact between the first leaf spring 27 and the second leaf spring 31 can be avoided. By forming the J-shaped tip bent portion 69 at the tips of the first leaf spring 27 and the second leaf spring 31, the interference avoidance distance can be easily secured without being restricted by the spring width.

In the manipulator 100, when a line passing through the first base end pin 47 and the second base end pin 49 and a line passing through the first tip pin 65 and the second tip pin 67 are parallel to each other on the same plane, the spaced distance between the first tip pin 65 and the second tip pin 67 is smaller than the spaced distance between the first base end pin 47 and the second base end pin 49. That is, the first leaf spring 27 and the second leaf spring 31 have a smaller spaced distance between the tips than the spaced distance between the base ends. Thus, the first leaf spring 27 and the second leaf spring 31 can rotate the rotating disk 63 at a large rotation angle in a smaller linear movement distance of the first link 25 and the second link 29, as compared to when the spaced distance between tips is larger than the spaced distance between the base ends. Further, the rotating disk 63 and the rocking disk 39 can be made compact by forming the disk small in the radial direction.

In the manipulator 100, the ultrasonic probe 43 can be mounted on the holder. That is, the manipulator 100 can be used for intra-operative laparoscopic ultrasonic diagnosis. The ultrasonic probe 43 mounted on the holder can rotate with two-degree-of-freedom about the pitch shaft 37 and the yaw shaft 41 by independent linear operations of the first link 25 and the second link 29. The ultrasonic probe 43 can acquire internal information of the target in real time by scanning along the surface of the target by the two-degree-of-freedom rotation.

Particularly, in the manipulator 100 using the two-degree-of-freedom rotation mechanism using parallel springs, it is possible to perform a rotation operation around the contact point of the target (operation to stroke the target surface) while realizing a compact tip shape, so ideal probe scanning is realized. The manipulator 100 can absorb reaction force from the target by the elasticity of the first leaf spring 27 and the second leaf spring 31, and make it possible to contact the ultrasonic probe 43 with an appropriate force to the target without giving an excessive load.

In the manipulator 100, the first leaf spring 27 and the second leaf spring 31 are made of a nickel titanium alloy. The nickel titanium alloy is biocompatible and has a super-elastic property. Therefore, in the manipulator 100 for intra-operative laparoscopic ultrasonic diagnosis using the twodegree-of-freedom rotation mechanism using parallel springs, while maintaining biocompatibility, it is possible to satisfy the rotation operation range 20° to 90° around the pitch shaft and the rotation operation range of ±90° around the yaw shaft required for ultrasonic diagnosis.

In the manipulator 100, the long first link 25 and the long second link 29 can be disposed without interfering with each other. When the two-degree-of-freedom rotation mechanism using parallel springs is used for the manipulator 100 for intra-operative laparoscopic ultrasonic diagnosis, the first link 25 and the second link 29 are accommodated in the outer cylinder 23. The outer cylinder 23 is inserted through the trocar that has passed through the incision of the abdomen. Therefore, it is necessary for the manipulator 100 to secure a distance (outer cylinder length) from the tip to the manipulator drive unit located outside within a predetermined length (for example, about 125 to 300 mm). By disposing the first link 25 and the second link 29 in parallel, it is easy to secure the outer cylinder length while avoiding mutual interference.

Next, the result of evaluating whether a testing machine has the rigidity necessary for performing ultrasonic diagnosis by manufacturing the testing machine of the manipulator 100 and evaluating its rigidity will be described.

In the test, with reference to contact force required for ultrasonic diagnosis on a body surface, if the rigidity value in the posture when the pitch shaft is rotated by 90° is about 1 to 6 N/mm, it is determined to have rigidity necessary for ultrasonic diagnosis.

Test Method

The rigidity value is calculated by measuring the amount of displacement when a load is applied to the tip of the testing machine which has rotated to each posture by a motion analysis microscope (for example, VW-6000, KEYENCE). Here, the pitch shaft rotation is measured after the posture is changed by 10° at a time in the range of 20° to 90°. In the measurement, considering that the load always acts in the vertical direction of the probe surface, the load is increased from 0 to 1.5 N by 0.5 N at a time, and then the load is removed to 0 N by 0.5 N at a time.

Since the testing machine is used by being inserted into the trocar, measurement is performed after the tip of the outer cylinder 23 is fixed to obtain an equivalent environment. Each posture is measured three times, with the measurement accuracy as 50 μm and the sampling rate as 60 FPS.

Figure 14:
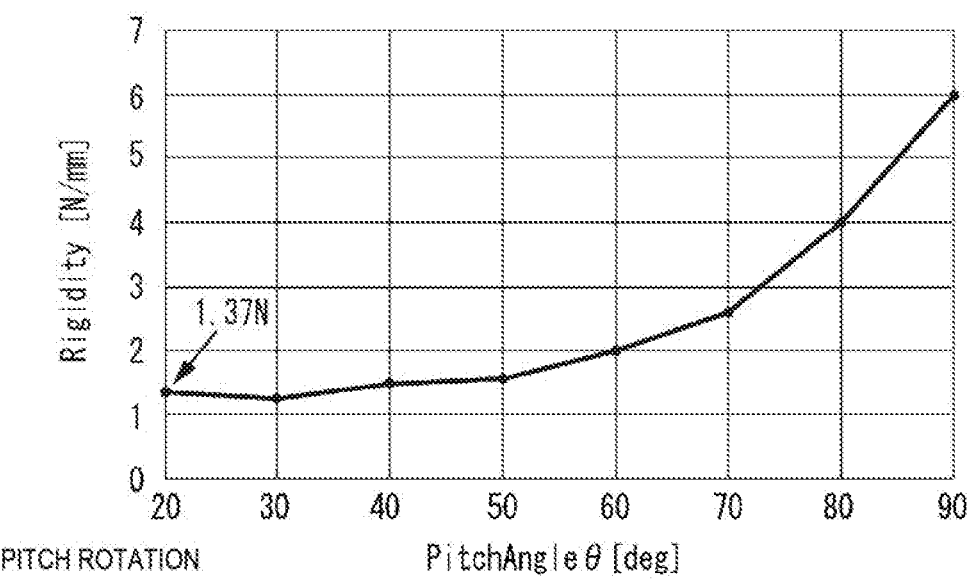
FIG. 14 is an explanatory diagram illustrating a result of rigidity evaluation performed on the manipulator.

FIG. 14 is an explanatory diagram illustrating the result of rigidity evaluation performed on the manipulator. As illustrated in FIG. 14, it is found that the result of the pitch shaft rotation is that the rigidity value at the representative pitch angle 20° is 1.37 N/mm, and satisfies the rigidity value 1 to 6 N/mm required for ultrasonic diagnosis.

Second Embodiment

Figure 15:
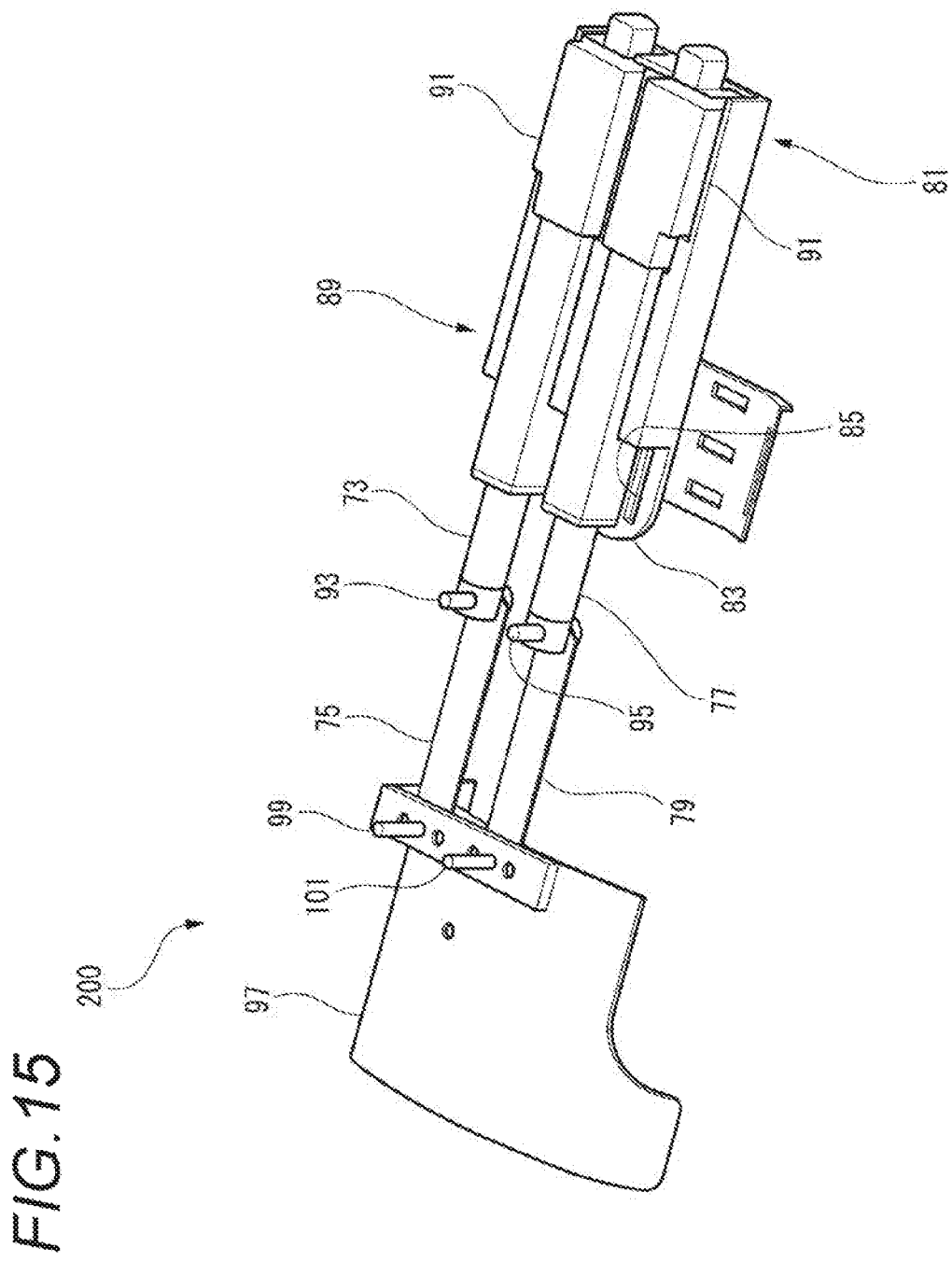
FIG. 15 is a perspective view of a forearm motion support device according to a second embodiment.

In a second embodiment, as an apparatus to which a two-degree-of-freedom rotation mechanism using parallel springs according to the present invention is applied, a forearm motion support device will be described as an example. FIG. 15 is a perspective view of the forearm motion support device according to the second embodiment.

A forearm motion support device 200 includes a base body, a first link 73, a first leaf spring 75, a second link 77, a second leaf spring 79, and a driven link.

In the forearm motion support device 200, the base body is a device body 81. The device body 81 includes a base plate 83 made of ABS resin. A belt hole 85 is formed in the base plate 83. The device body 81 is attached to a forearm by winding a belt 87 passed through the belt hole 85 of the base plate 83. A linear motion unit 89 is provided on the upper surface of the base plate 83. The linear motion unit 89 includes a pair of linear motion motors 91. The linear motion unit 89 supports the first link 73 and the second link 77 so as to freely advance and retract.

The first link 73 is capable of advancing and retracting in the longitudinal direction of the first link 73 with respect to the device body 81 by one linear motion motor 91 of the linear motion unit 89. A rotational motion of the linear motion motor 91 is, for example, converted into linear motion by a ball screw mechanism and transmitted to the first link 73.

The first leaf spring 75 is formed in a rectangular shape. The longitudinal base end of the first leaf spring 75 is connected to the tip of the first link 73 as a rotation pair by a first base end pin 93. The first base end pin 93 passes through the longitudinal base end of the first leaf spring 75 in the thickness direction.

The second link 77 is disposed with the first link 73 side by side. The second link 77 is capable of advancing and retracting in the longitudinal direction of the second link 77 with respect to the device body 81 by the other linear motion motor 91 of the linear motion unit 89. A rotational motion of the linear motion motor 91 is, for example, converted into linear motion by a ball screw mechanism and transmitted to the second link 77.

The second leaf spring 79 is formed in the same rectangular shape as the first leaf spring 75. The longitudinal base end of the second leaf spring 79 is connected to the tip of the second link 77 as a rotation pair by a second base end pin 95 in the same direction as the first base end pin 93. The second base end pin 95 passes through the longitudinal base end of the second leaf spring 79 in the thickness direction.

In the forearm motion support device 200, the first leaf spring 75 and the second leaf spring 79 can have dimensions of a length of 50 mm (a pitch length of the pin hole 71) in the longitudinal direction, a width of 10 mm, and a thickness of 0.5 mm considering the operation and the rigidity of the mechanism. In the forearm motion support device 200, hardened carbon steel can be used for the first leaf spring 75 and the second leaf spring 79.

In the forearm motion support device 200, the driven link is a hold plate 97 made of ABS resin. The hold plate 97 is attached by winding the belt 87 around the back of the hand. The tips of the first leaf spring 75 and the second leaf spring 79 are connected to the hold plate 97 as a rotation pair. That is, the tip of the first leaf spring 75 is connected to the hold plate 97 as a rotation pair by a first tip pin 99 in the same direction as the first base end pin 93. Further, the tip of the second leaf spring 79 is connected to the hold plate 97 as a rotation pair by a second tip pin 101 in the same direction as the second base end pin 95.

In the forearm motion support device 200, the device body 81 which is the base body is attached and fixed to the forearm, and the hold plate 97 which is the driven link is attached and fixed between a wrist and a base of fingers.

Next, the operation of the above configuration will be described.

Figure 16:
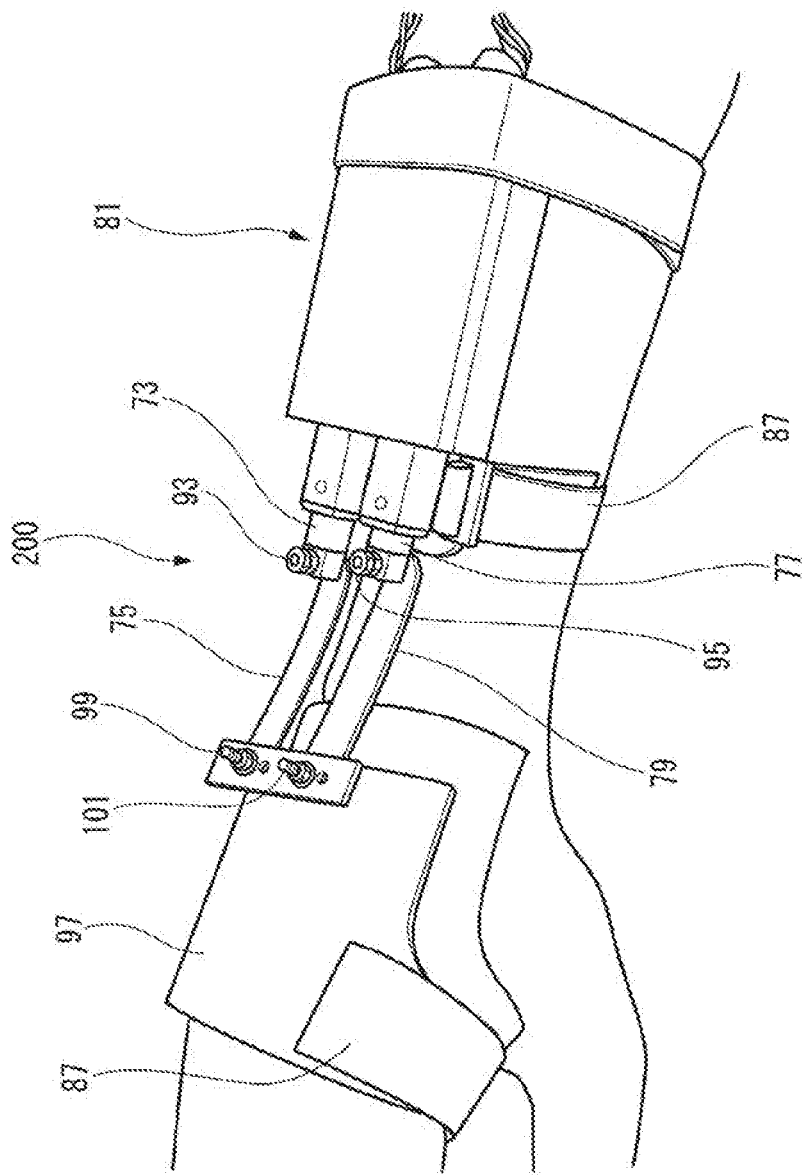
FIG. 16 is a perspective view of a state in which the forearm motion support device illustrated in FIG. 15 is attached to the forearm and the hand is dorsiflexed.

FIG. 16 is a perspective view of a state in which the forearm motion support device illustrated in FIG. 15 is attached to the forearm and the hand is dorsiflexed. In the forearm motion support device 200, the device body 81 is attached to the forearm and the hold plate 97 is attached to the back of the hand or the like. When the first link 73 and the second link 77 advance, the hand is palm-flexed through the wrist. When the first link 73 and the second link 77 retract, the hand is dorsiflexed through the wrist.

Figure 17:
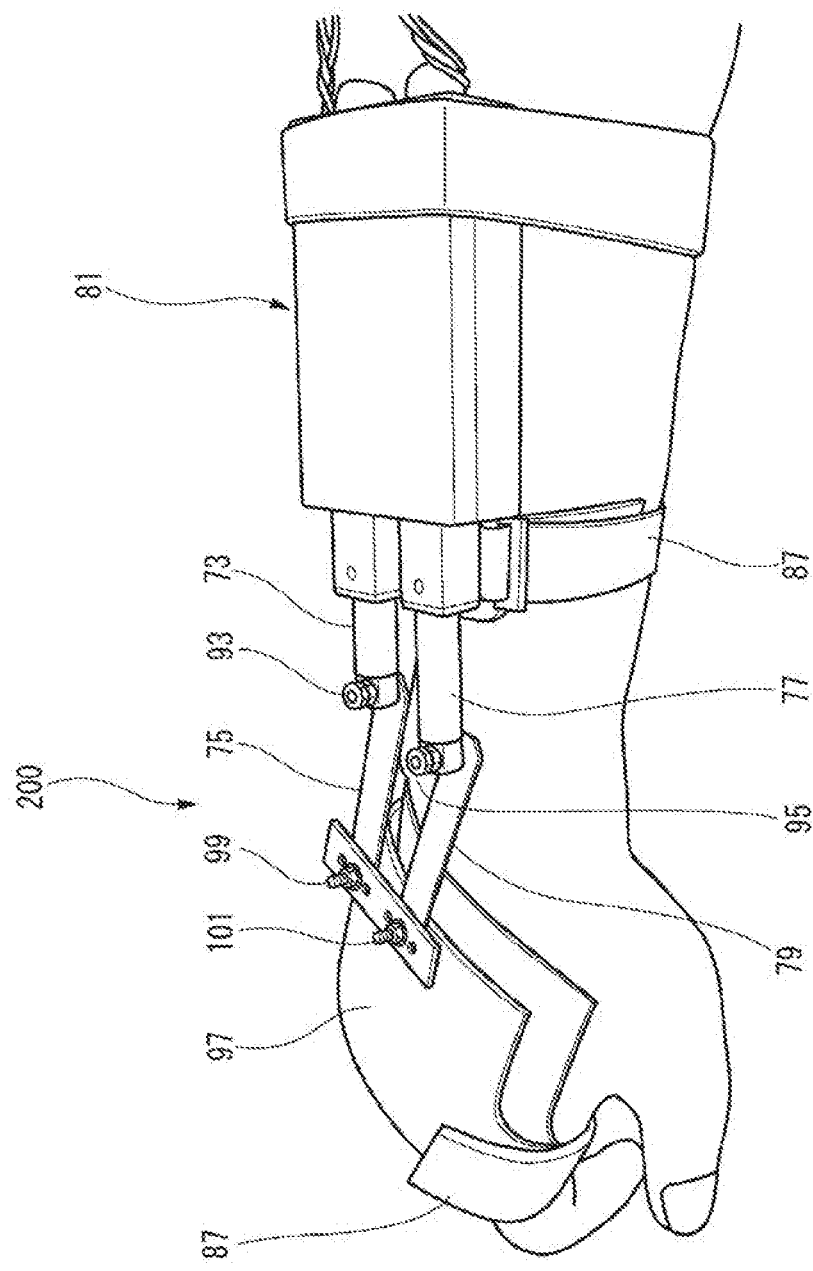
FIG. 17 is a perspective view of a state in which the forearm motion support device illustrated in FIG. 15 is attached to the forearm and the hand is abducted.

FIG. 17 is a perspective view of a state in which the forearm motion support device illustrated in FIG. 15 is attached to the forearm and the hand is abducted. In the forearm motion support device 200, when making difference (moving with difference) in the advance and retreat amounts of the first link 73 and the second link 77, the hand is abducted or adducted.

The first link 73 and the second link 77 can be moved with difference while advancing or retracting. In this case, the palm can be operated to stroke the target (for example, a product held by the palm or a part touched by the palm) while applying contact pressure to the target. In this manner, the two-degree-of-freedom rotation mechanism using parallel springs can be used as the forearm motion support device 200 for performing a forearm motion support operation. In the forearm motion support device 200 using the two-degree-of-freedom rotation mechanism using parallel springs, since the first leaf spring 75 and the second leaf spring 79 are included as a chain, the reaction force received from the driven link is absorbed by the deformation of the first leaf spring 75 and the second leaf spring 79, and thus it is possible to prevent application of an excessive load to the wrist joint.

The forearm motion support device 200 can realize a two-degree-of-freedom operation by the motion of the two linear motion motors 91. By operating the two springs of the first leaf springs 75 and the second leaf springs 79 in the same direction, it is possible to support abduction and adduction by operating palmar flexion and dorsiflexion.

It is known that movement of the rotation center occurs in the wrist joint. Since the forearm motion support device 200 has two-degree-of-freedom, it is possible to drive the driven link according to the motion of the rotation center. Since springs are included as elements of the chain of the link mechanism, it is possible to support the movement without applying a physical load to a wearer. The forearm motion support device 200 is thin, particularly at parts that use springs, and can transmit power along the wearer's body surface. From this, the forearm motion support device 200 also has an advantage that it is possible to prevent the disturbance of the wearer's motion.

According to the forearm motion support device 200, since two spring elements are used for the chain, it is possible to support the motion of a single joint with two-degree-of freedom while it is compact, lightweight, and safe. The forearm motion support device 200 also has advantages such as simplification of mechanism, reduction in the number of parts, acceptance of motion deviation between the human body and the device, and the like by using spring elements for mechanism joint parts.

Next, a result obtained by manufacturing the testing machine of the forearm motion support device 200 and measuring output for evaluation of the testing machine is illustrated.

Test Method

Using the FEM analysis, the assist torque obtained in the wrist joint is analyzed by the testing machine. Analysis is performed when the hand is in the normal position (posture in which the major shaft of the middle finger and the forearm are parallel).

Figure 18:
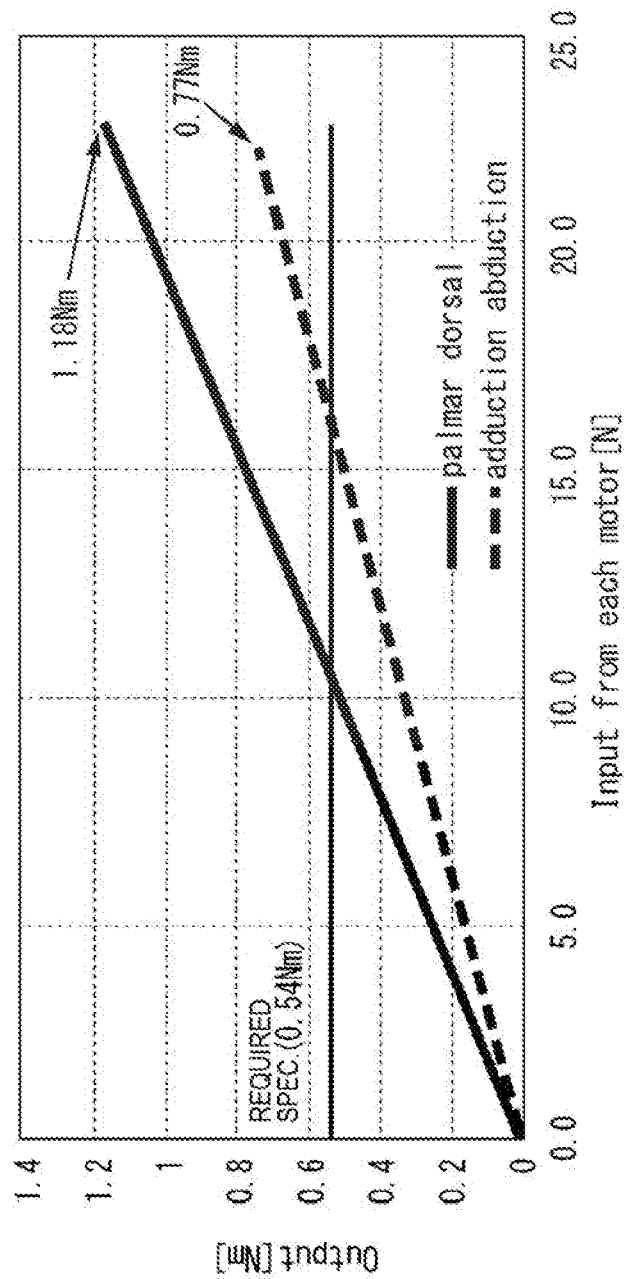
FIG. 18 is an explanatory view illustrating a result of output measurement performed on the forearm motion support device.

FIG. 18 is an explanatory view illustrating the result of output measurement performed on the forearm movement support device. When the testing machine applies the rated output to the linear motion motor 91, it is checked that the output is 0.77 Nm for abduction and adduction, and the output is 1.18 Nm for palmar flexion and dorsiflexion. The average torque at the wrist joint required for lifting the hand of a Japanese elderly man is 0.54 Nm for both movements, and it becomes clear that the hand can be lifted by the testing machine.

Therefore, the two-degree-of-freedom rotation mechanism using parallel springs (the manipulator 100, the forearm motion support device 200) of the present embodiment is lightweight, has a small number of parts and a simple structure, is capable of operating a driven link with two-degree-of-freedom at low cost, is excellent in sterilizing and disinfecting property, and does not apply excessive burden to the target.

While exemplary embodiments have been described with reference to the drawings, it is to be understood that the present invention is not limited thereto. It is apparent to those skilled in the art that changes and modifications are conceivable within the scope described in the claims, and it would be appreciated that those naturally belong to the technical scope of the present invention.

For example, in the configuration example of the first embodiment, the case where the ultrasonic probe holder is fixed to the yaw shaft has been described as an example, but the two-degree-of-freedom rotation mechanism using parallel springs may be configured such that a holder for the other end effector is fixed to the yaw shaft. In this case, examples of the end effector include a clamp, a capturing device, scissors, and a stapler.

In the second embodiment, the example in which the forearm motion support device 200 is fixed to the wrist and used has been described, but it may be used by being fixed to an ankle, without being limited to the example in which it is fixed to the wrist. In this case, the device body 81 is mounted near the ankle of a leg, and the hold plate 97 is attached and fixed between the ankle and a base of toes. When the first link 73 and the second link 77 advance, the foot bends forward through the ankle. When the first link 73 and the second link 77 retract, the foot is dorsiflexed through the ankle.

The first link 73 and the second link 77 can be moved with difference while advancing or retracting. In this case, the foot can be operated to stroke the target (for example, a product pressed by the foot or a part touched by the foot) while applying contact pressure to the target. In this manner, the two-degree-of-freedom rotation mechanism using parallel springs can perform a motion support operation to one foot or both feet. According to the two-degree-of-freedom rotation mechanism using parallel springs, since the chain includes the first leaf spring 75 and the second leaf spring 79, the reaction force received from the driven link is absorbed by the deformation of the first leaf spring 75 and the second leaf spring 79, and it is possible to prevent the excessive load applied to the ankle joint.

In addition to the example of being fixedly used on the ankle, the forearm motion support device 200 may be attached and fixed to peripheral parts of joints of a human body (it may be an animal other than a human body, the same applies below). Examples of the joints of the human body include parts such as shoulder, finger, elbow, knee, neck, backbone (spine), and ankle joint. In this case, the hold plate 97 is attached and fixed between the two portions sandwiching the above-described peripheral part of the joint of a human body. Thereby, it is possible to expect the same effect as in the case where the forearm motion support device 200 is fixed to the wrist, and it is possible to support the motion around the joint part for a disabled person, for example.

The present application is based on Japanese Patent Application No. 2016-113880 filed on Jun. 7, 2016, the entire contents of which are incorporated by reference in the present application.

INDUSTRIAL APPLICABILITY

The present invention is useful as the two-degree-of-freedom rotation mechanism using parallel springs which is lightweight, has a small number of parts and a simple structure, is capable of operating a driven link with two-degree-of-freedom at low cost, is excellent in sterilizing and disinfecting property, and does not apply excessive burden to a target.

The invention claimed is:

1. A two-degree-of-freedom rotation mechanism using parallel springs, the mechanism comprising:
  a base body;
  a first link that is supported to be capable of advancing and retracting in a longitudinal direction of the first link with respect to the base body, a tip end of the first link having a first through hole, the first through hole extending along a first direction, the first direction being orthogonal to the longitudinal direction of the first link;
  a first leaf spring of a rectangular shape of which a longitudinal base end is connected to the tip of the first link as a rotation pair by a first base end pin inserting into the first through hole;
  a second link that is arranged with the first link side by side along a second direction, and is supported to be capable of advancing and retracting in a longitudinal direction of the second link with respect to the base body, a tip end of the second link having a second through hole, the second through hole extending along the first direction, the first direction being orthogonal to the longitudinal direction of the second link;
  a second leaf spring of a rectangular shape of which a longitudinal base end is connected to the tip of the second link as a rotation pair by a second base end pin inserting into the second through hole; and
  a driven link that is connected to a tip of the first leaf spring as a rotation pair by a first tip pin in the same direction as the first base end pin and connected to a tip of the second leaf spring as a rotation pair by a second tip pin in the same direction as the second base end pin,
  wherein the second direction is orthogonal to the first direction and the longitudinal direction of the second link, and
  the first and second base end pins are inserted into the first and second through holes, respectively, in the same direction along the first direction.

2. The two-degree-of-freedom rotation mechanism using parallel springs according to claim 1, the mechanism further comprising:
  a first support rod including a base end fixed to the base body and extending along the first link and the first leaf spring;
  a second support rod including a base end fixed to the base body and extending along the second link and the second leaf spring;
  a pitch shaft including both ends supported by tips of the first support rod and the second support rod;
  a rocking disk having a rotation axis extending in a direction parallel to a diameter of the rocking disk and being rotatably supported around the pitch shaft;
  a yaw shaft which is rotatably supported on the rocking disk in a vertical direction; and
  a holder which is fixed to one end of the yaw shaft and is rotatable regarding the rocking disk, wherein
  the driven link is a rotating disk fixed to the other end of the yaw shaft and rotatable regarding the rocking disk.

3. The two-degree-of-freedom rotation mechanism using parallel springs according to claim 2, wherein
  the first leaf spring and the second leaf spring are provided with J-shaped tip bent portions bent in a direction in which the tips thereof approach each other.

4. The two-degree-of-freedom rotation mechanism using parallel springs according to claim 2, wherein
  the first leaf spring and the second leaf spring have a smaller spaced distance between the tips than a spaced distance between the base ends.

5. The two-degree-of-freedom rotation mechanism using parallel springs according to claim 2, wherein
  the holder detachably holds an ultrasonic probe.

6. The two-degree-of-freedom rotation mechanism using parallel springs according to claim 1, wherein
  the first leaf spring and the second leaf spring are made of a nickel titanium alloy.

7. The two-degree-of-freedom rotation mechanism using parallel springs according to claim 1, wherein
  the first link and the second link are parallel.

8. The two-degree-of-freedom rotation mechanism using parallel springs according to claim 1, wherein
  the base body is adapted to be attached and fixed to a peripheral portion of a joint of a human body, and
  the driven link is adapted to be attached and fixed between a first portion of the peripheral portion of the joint of the human body and a second portion of the peripheral portion of the joint of the human body.

9. The two-degree-of-freedom rotation mechanism using parallel springs according to claim 8, wherein
  the peripheral portion of the joint of the human body is a forearm, and
  the first portion is a wrist, and the second portion is a base of fingers.

* * * * *